United States Patent [19]

Shimotori et al.

[11] Patent Number: 5,104,886

[45] Date of Patent: Apr. 14, 1992

[54] AMIDE DERIVATIVES, PROCESSES FOR PRODUCTION THEREOF, AND AGRICULTURAL-HORTICULTURAL FUNGICIDE CONTAINING THEM

[75] Inventors: Hitoshi Shimotori; Yoshiro Kanemoto; Hideo Yamazaki; Tsutomu Ishii; Shuji Ozawa, all of Yokohama; Yuji Yanase, Kamakura; Toshiaki Kuwatsuka, Mobara; Yoshinori Tanaka, Yokohama; Takeshi Sekine, Hiratsuka; Keiko Shinada, Yokohama, all of Japan

[73] Assignee: Mitsui Toatsu Chemicals, Inc., Tokyo, Japan

[21] Appl. No.: 545,026

[22] Filed: Jun. 28, 1990

Related U.S. Application Data

[62] Division of Ser. No. 259,817, Oct. 19, 1988, Pat. No. 4,980,363.

[30] Foreign Application Priority Data

Oct. 23, 1987 [JP] Japan .................. 62-267827
Jul. 13, 1988 [JP] Japan .................. 63-172639
Aug. 8, 1988 [JP] Japan .................. 63-196184
Aug. 31, 1988 [JP] Japan .................. 63-216699

[51] Int. Cl.$^5$ .................................. A01N 43/78
[52] U.S. Cl. ...................................... 514/365
[58] Field of Search .......................... 514/365

[56] References Cited

U.S. PATENT DOCUMENTS 4,552,887 11/1985 Kay .................... 514/381
4,918,089 4/1990 Kusaba ................ 514/365

Primary Examiner—Robert Gerstl
Attorney, Agent, or Firm—Millen, White & Zelano

[57] ABSTRACT

An amide derivative represented by the following general formula (I)

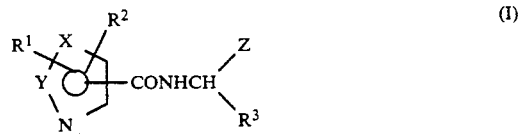

wherein one of X and Y represents a sulfur atom and the other represents a carbon atom, Z represents a nitrile or thioamide group, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group, or an unsubstituted or halosubstituted phenyl group;

processes for producing the amide derivative; an agricultural-horticultural fungicide comprising the amide derivative as an active ingredient; and to an agricultural-horticultural fungicidal composition comprising the amide derivative of general formula (I) as an active ingredient.

10 Claims, No Drawings

AMIDE DERIVATIVES, PROCESSES FOR PRODUCTION THEREOF, AND AGRICULTURAL-HORTICULTURAL FUNGICIDE CONTAINING THEM

This is a division, of application Ser. No. 07/259,817 filed Oct. 19, 1988, now U.S. Pat. No. 4,980,363.

BACKGROUND OF THE INVENTION

This invention relates to an amide derivative represented by the following general formula (I)

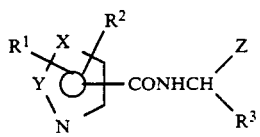

wherein one of X and Y represents a sulfur atom and the other represents a carbon atom, Z represents a nitrile or thioamide group, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group, or an unsubstituted or halo-substituted phenyl group;
processes for producing the amide derivative; an agricultural-horticultural fungicide comprising the amide derivative as an active ingredient; and to an agricultural-horticultural fungicidal composition comprising the amide derivative of general formula (I) as a first active ingredient and at least one member selected from the group consisting of acylalanine fungicides having the action of controlling plant diseases caused by Oomycetes, dithiocarbamate fungicides, N-haloalkylthioimide fungicides inorganic copper fungicides, tetrachloroisophthalonitrile, dichlofluanide and fluazinam.

Heretofore, compounds having various chemical structures have been used as agricultural-horticultural fungicides, and greatly contributed to the control of plant diseases and consequently to the development of agriculture. But these conventional fungicidal chemicals have not proved to have sufficient controlling activity and safety. For example, some of dithiocarbamate fungicides such as zinc ethylenebis(dithiocarbamate) [zineb], manganese ethylenebis(dithiocarbamate) [maneb], a complex of manganese ethylenebis(dithiocarbamate) and zinc ethylenebis(dithiocarbamate [mancozeb] and dizinc bis(dimethyldithiocarbamate) ethylenebis(dithiocarbamate) [polycarbamate], N-haloalkyl thioimide fungicides such as N-trichloromethylthio-4-cyclohexene-1,2-dicarboximide [captan], N-1',1',2',2'-tetrachloroethylethio-4-cyclohexene-1,2-dicarboximide [captafol] and N-trichloromethylthiophthalimide [folpet], inorganic copper fungicides such as cupric sulfate, basic cupric sulfate, basic cupric chloride and cupric hydroxide, tetrachloroisophthalonitrile [TPN], N-(dichlorofluoromethylthio)-N',N-dimethyl-N-phenylsulfamide[dichlofluanide] and 3-chloro-N-(3-chloro-5-trifluoromethyl-2-pyridyl)-2,6-dinitro-4-trifluoromethylaniline [fluazinam] show an outstanding control efficacy on diseases of plants such as fruit trees and vegetables and are widely used as agricultural-horticultural fungicides. However, these chemicals mainly exhibit a preventive effect and are not expected to produce a curative effect. Hence, they have the serious defect that when a plant disease is seen to occur, these chemicals are not expected to give a sufficient efficacy. When chemical application for controlling plant diseases is considered in an actual situation, the chemicals are more or less sprayed after the occurrence of plant disease symptons, and the abovecited chemicals are difficult of controlling the diseases completely. Furthermore, the concentrations of these chemicals at which they exhibit a control effect are very high so that they are difficult to use safely, and some of these chemicals have an unnegligible toxicity to fish.

In order to eliminate these defects, extensive research work has been done on new controlling agents. For example, acylalanine fungicides, such as N-(2,6-dimethylphenyl)-N-(2'-methoxyacetyl)alanine methyl ester [metalaxyl], N-(2,6-dimethylphenyl)-N-(2-furoyl)alanine methyl ester [furalaxyl], N-(2,6-dimethylphenyl)-N-(phenylacetyl)alanine methyl ester [benalaxyl], (2-chloro-N-(2,6-dimethylphenyl)-N-(tetrahydro-2-oxo-3-furanyl)acetamide [ofurace] and 2-methoxy-N-(2,6-dimethylphenyl)-N-(2-oxo-1,3-oxazolidin-3-yl)acetamide [oxadixyl] were developed as controlling agents on plant diseases caused by Oomycetes which also have an excellent curative effect have been developed and come into practical use worldwide. It has already been pointed out that resistant strain to these chemicals have appeared and their control effect have consequently decreased.

Many active benzylamide compounds have been discovered and used as herbicides or fungicides. For example, known substituted benzamide derivatives include ethyl N-benzoyl-N-(3,4-dichlorophenyl)-2-aminopropionate [benzoylprop ethyl] as herbicide, and N-(3-isopropoxyphenyl)-2-methylbenzamide [mepronil] as fungicide.

BP-2094786, BP-2095237, and BP-2107308 disclose a herbicide and a fungicide comprising a substituted benzylamide derivative having a 4-pyridylcarbonyl, 2-furylcarbonyl, 2-thienylcarbonyl or 2-benzofurylcarbonyl group, but its phytotoxicity on crop plants is a problem.

It is an object of this invention to provide a compound being free from the above-mentioned defects of the prior art and having excellent properties as an agricultural-horticultural fungicide; processes for production thereof, and an agricultural-horticultural fungicide comprising the compound as an active ingredient, and an agricultural-horticultural fungicidal composition comprising the compound as a first active ingredient and a specific known fungicidal compound as a second active ingredient. More specifically, the invention provides a compound which has a preventive and a curative effect on a wide range of plant diseases such as diseases of fruit trees and vegetables, shows an excellent control effect against resistant fungi, has a wide range of applicability and a long residual effect, does not show phytotoxicity on crop plants, and possesses very low toxicity on warm-blooded animals and fish; simple processes for production thereof in high yields; an agricultural-horticultural fungicide comprising the compound as an active ingredient; and an agriculturalhorticultural fungicidal composition comprising the compound as a first ingredient and a specific known fungicidal compound as a second active ingredient.

We worked extensively on acylamide derivatives in order to achieve the above object, and have found that amide derivatives having a thiazole or isothiazole ring have biological activity which cannot at all be anticipated from the above-exemplified compounds and an excellent controlling effect on a wide range of plant diseases; and that particularly, these amide derivatives have both a preventive and a curative effect in controlling various crop diseases such as late blight and downy mildew.

SUMMARY OF THE INVENTION

Thus, according to this invention, there is first provided an amide derivative represented by the following general formula (I)

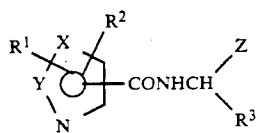
(I)

wherein one of X and Y represents a sulfur atom and the other represents a carbon atom, Z represents a nitrile or thioamide group, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group, or an unsubstituted or halo-substituted phenyl group.

In the amide derivative of general formula (I), examples of the alkyl group for $R^1$ and $R^2$ are methyl, ethyl, n-propyl, iso-propyl, n-butyl, i-butyl, sec-butyl, tert-butyl, n-pentyl and n-hexyl groups. Examples of the halomethyl group are chloromethyl and trifluoromethyl groups. The alkenyl group for $R^3$ is, for example, a vinyl, allyl, propen-1-yl, 2-methylpropen-1-yl, 1-methylpropen-1-yl, 1,2-dimethylpropen-1-yl, 2-ethylpropen-1-yl or 2-n-propylpropen-1-yl group. The haloalkenyl group is, for example, a 2-chloroethenyl, 2-chloropropen-1-yl, or 1-methyl-2-chloropropen-1-yl group. Examples of the alkoxy group are methoxy, ethoxy, n-propoxy, iso-propoxy, n-butoxy, sec-butoxy and tert-butoxy groups. Examples of the alkylthio group are methylthio, ethylthio, n-propylthio i-propylthio, n-bytylthio, i-butylthio, sec-butylthio and tert-butylthio groups. Examples of the alkynyloxy group are propyn-2-yloxy, 3-methylpropyn-2-yloxy and 3-ethylpropyn-2-yloxy groups. Examples of the alkynylthio groups are propyn-2-ylthio, 3-methylpropyn-2-ylthio, 3-ethyl propyn-2-ylthio groups. The halogen atom may be, for example, fluorine, chlorine, bromine or iodine.

The compound of general formula (I) is a novel compound.

The present invention also provides
a process for producing an amide derivative represented by the following general formula (IV)

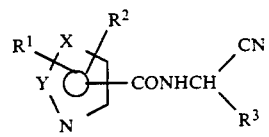
(IV)

wherein one of X and Y represents a sulfur atom and the other represents a carbon atom, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group or an unsubstituted or halogen-substituted phenyl group, which comprises reacting a heterocyclic 5-mebered carboxylic acid represented by the following general formula (II)

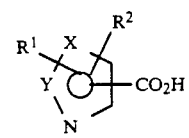
(II)

wherein X, Y, $R^1$ and $R^2$ are as defined above, or its reactive derivative with an aminoacetonitrile represented by the following general formula (III)

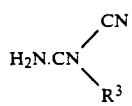
(III)

wherein $R^3$ is as defined above, or its salt;
a process for producing an amide derivative represented by the following general formula (IV)

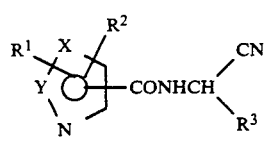
(IV)

wherein one of X and Y represents a sulfur atom and the other represents a carbon atom, each of $R^1$ and $R^2$ represents a hydrogen atom, a halogen atom, an alkyl group having 1 to 6 carbon atoms, a halomethyl group or a phenyl group, and $R^3$ represents an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, or a pyrazolyl group, which comprises halogenating an N-cyanomethylcarboxylic acid amide represented by the following general formula (V)

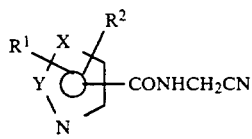 (V)

wherein X, Y, R¹ and R² are as defined above, 20 to form an intermediate represented by the following general formula (VI)

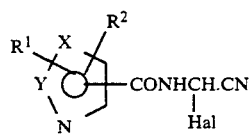 (VI)

wherein X, Y, R¹ and R² are as defined above, and Hal represents a halogen atom,
and then reacting the compound of general formula (VI) with a compound represented by the following general formula (VII)

$HR^3$ (VII)

wherein $R^3$ is as defined above; and
a process for producing a compound represented by the following general formula (VIII)

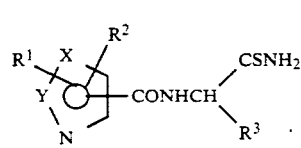 (VIII)

wherein X and Y represent a sulfur or carbon atom, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group or an unsubstituted or halogen-substituted phenyl group,
which comprises subjecting a compound represented by the following general formula (IV)

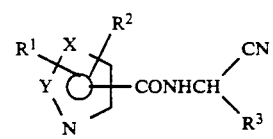 (IV)

are as defined
wherein X, Y, R¹, R² and R³ are as defined above,
to addition-reaction with hydrogen sulfide.

Detailed Description p The processes for producing the amide derivatives of the invention are shown by the following reaction schemes (a) to (c).

Reaction scheme (a)

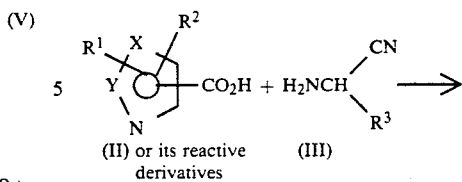

(II) or its reactive derivatives (III)

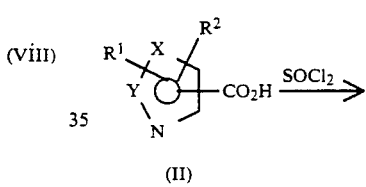 (IV)

In this scheme, the amide derivative of general formula (IV) can be produced by reacting the heterocyclic 5-membered carboxylic acid of general formula (II) or its reactive derivative (such as an acid chloride or an acid anhydride) with the aminoacetonitrile of general formula (III) or its salt. Various methods are available in performing the reaction in scheme (a), and will be described below with reference to the following reaction schemes (a)-1 to (a)-5.

Reaction scheme (a)-1
Method comprising converting the carboxylic acid into a chloride and reacting it with the aminoacetonitrile:

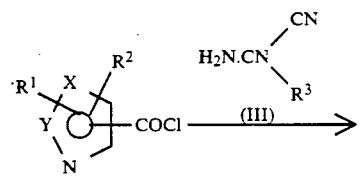

(II)

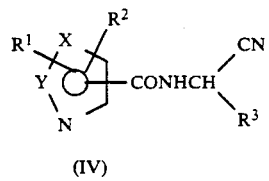

(IV)

Usually, the carboxylic acid derivative (II) is heated in an excess of thionyl chloride. After the reaction, the excess of thionyl chloride is evaporated to obtain the acid chloride. Sometimes, the reaction does not proceed well in thionyl chloride. In such a case, the carboxylic acid (II) is treated with a nearly equivalent weight of phosphorus pentachloride in an inert solvent. This makes the reaction proceed smoothly. After the reaction, low-boiling materials are evaporated to give the acid chloride. The resulting acid chloride is reacted in an inert solvent with the aminoacetonitrile (III) or its salt in the presence of an equivalent weight, or a slightly excessive amount, of a base to give the amide derivative (IV) easily. When the salt of the aminoacetonitile is used, the base is additionally supplied in an amount required to neutralize the salt. The inert solvent is inert to the chloride and the aminoacetonitrile. Specific examples are ethers such as diethyl ether, diisopropyl ether, tetrahydrofuran and dioxane, hydrocarbons such as benzene, toluene, xylene and ligroin, halogenated hydrocarbons such as dichloromethane, chloroform and carbon tetrachloride, esters such as ethyl acetate and ethyl propionate, and aprotic polar solvents such as N,N-dimethylformamide, dimethyl sulfoxide and 1,3-dimethylimidazolidinone. Pyridine may be used as the base and the solvent. Examples of the base may be organic bases such as triethylamine, dimethylaniline, pyridine and DBU, and inorganic bases such as ammonia, potassium hydrogen carbonate, potassium carbonate, sodium carbonate, sodium hydrogen carbonate, sodium hydroxide and ammonium carbonate, although these examples are not limitative. It is not desirable to perform this reaction at too high temperatures because the thermal stability of the intermediate aminoacetonitrile derivative (III) is low. Preferred reaction temperatures are 10° to 50° C. After the dropwise addition of the aminoacetonitrile derivative (III), the mixture is continuously stirred at room temperature in order to complete the reaction. The reaction time, which varies depending upon the reaction temperature, is usually 0.5 to 4 hours. After the reaction, the crude reaction product is obtained by a customary method. The resulting desired amide derivative can be easily isolated and purified by a conventional method such as recrystallization or column chromatography.

Reaction scheme (a)-2

Method comprising reacting an anhdyride of the carboxylic with the amino-itonitrile.

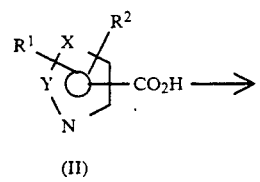

(II)

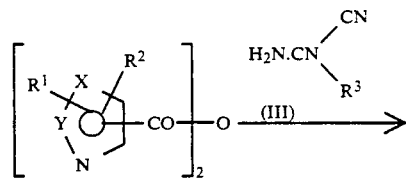

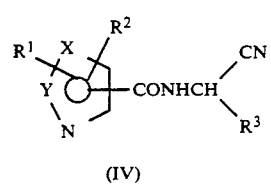

(IV)

The amide derivative (IV) can be obtained by carrying out the same reaction as in reaction scheme (a)-1 except that the acid anhydride is used instead of the acid chloride.

Reaction scheme (a)-3

Method comprising reacting a mixed acid anhydride of the carboxylic acid with the aminoacetonitrile.

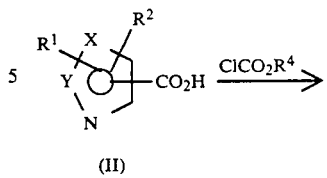

(II)

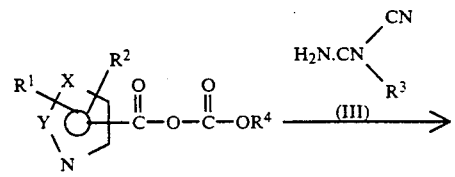

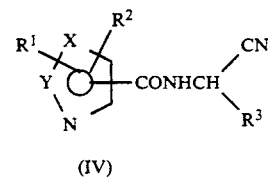

(IV)

(In the above scheme, $R^4$ represents a lower alkyl group.)

The carboxylic acid derivative (II) is dissolved in an organic solvent, and in the presence of a base, a chloroformate ester is added to form a mixed acid anhydride. Addition of the aminoacetonitrile (III) to the mixed acid anhydride gives the amide derivative (IV). The organic solvent and the base may be quite the same as those used in the reaction of scheme (a)-1. The reaction temperature is −50° to 20° C., preferably −10° to 10° C., for the reaction of the carboxylic acid with the chloroformate, and 0° to 50° C., preferably 10° to 30° C., for the reaction of the mixed anhydride with the aminoacetonitrile. The isolation and purification of the final product can be easily carried out in accordance with a conventional method as in the case of reaction scheme (a)-1.

Reaction scheme (a)-4

Method comprising using carbonyldiimidazole (CDI).

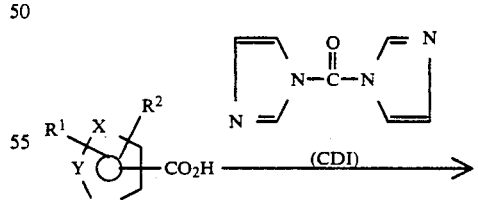

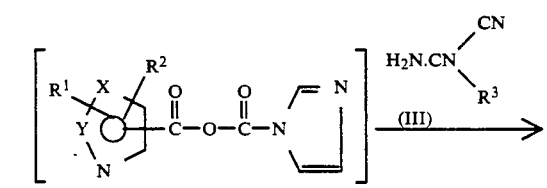

-continued

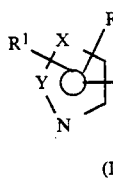

(IV)

The carboxylic acid derivative (II) is dissolved in an organic solvent, and carbonyldiimidazole is added. Then, at 0° to 50° C., preferably 0° to 30° C., the aminoacetonitrile (III) is added to give the amide derivative (IV). The organic solvent used may be the same as that used in the reaction of reaction scheme (a)-1. The isolation and purification of the final product can be easily carried out in a customary manner in the same way as described with regard to the reaction in reaction scheme (a)-1.

Reaction scheme (a)-5

Method comprising using dicyclohexylcarbodiimide (DCC).

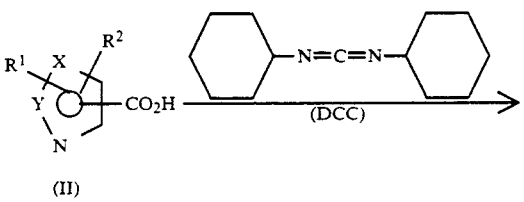

(II)

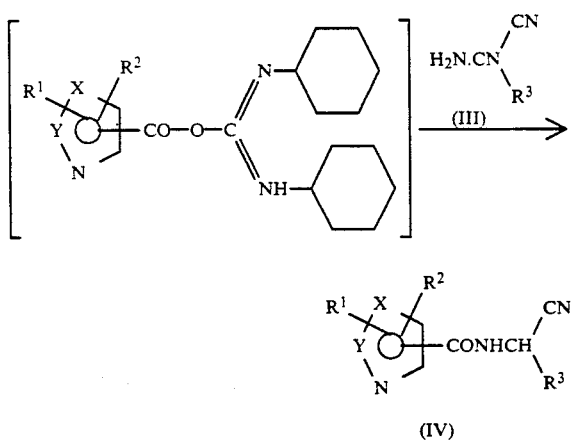

(IV)

The carboxylic acid derivative (II) is dissolved in an organic solvent, and dicyclohexylcarbodiimide is added to the solution. While the solution is cooled with ice water, the aminoacetonitrile (III) is added to give the amide derivative. The organic solvent used in this reaction may be the same as those exemplified with regard to reaction scheme (a)-1. The isolation and purification of the final product can be carried out easily by a conventional method.

In addition to the reactions shown in reaction schemes (a)-1 to (a)-5, methods usually employed in the field of peptide synthesis may be used for the production of the amide derivatives of the invention.

Where R³ in general formula (IV) is an alkoxy, alkylthio, alkynyloxy, alkynylthio or pyrazolyl group, the amide derivative (IV) can be produced by the following process (b).

Process (b)

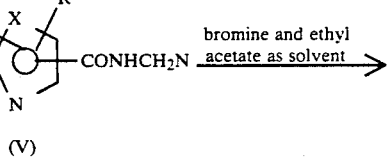

(V)

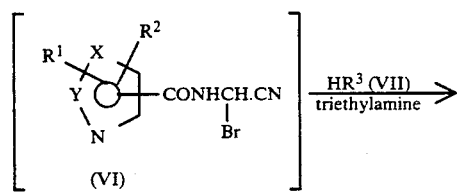

(VI)

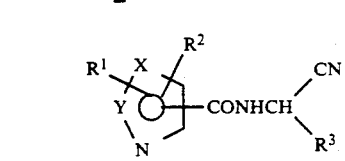

(IV)

An N-cyanomethylcarboxylic acid amide (V) corresponding to formula (IV) in which $R^3$ is a hydrogen atom is very important as a synthesis intermediate for a compound of general formula (IV) in which $R^3$ represents an alkyloxy, alkylthio, alkynyloxy, alkynylthio or pyrazolyl group.

Treatment of the N-cyanomethylcarboxylic acid amide (V) with a halogenating agent in a suitable solvent gives a halogenated intermediate (VI). Bromine or N-bromosuccimide may be used as the halogenating agent. Examples of the solvent are aliphatic halogenated hydrocarbons such as dichloromethane, chloroform, carbon tetrachloride and 1,4-dichloroethane, and aliphatic carboxylic acid esters such as methyl acetate, ethyl acetate, isopropyl acetate and ethyl propionate. The reaction temperature is 20° to 80° C., preferably 30° to 50° C. This reaction may be carried out in an atmosphere of an inert gas. Since the halogenation intermediate (VI) is unstable, it is immediately reacted with $HR^3$ (VII). This reaction is carried out in the presence of an acid acceptor. Examples of the acid acceptor are tertiary amines such as triethylamine and dimethylaniline, although they are not limitative. Desirably, this reaction is carried out in a solvent or diluent. It is desirable to avoid high temperatures in carrying out this reaction because the thermal stability of the intermediate is low. Desirably, it is carried out under cooling because it is exothermic. The desired amide derivative (IV) may be purified in a customary manner by recrystallization, column chromatography, etc.

A compound of formula (VIII) corresponding to a compound (I) in which Z is a thioamide group may be carried out by the following process (c).

Process (c)

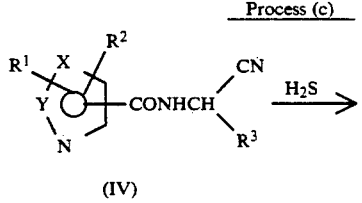

(IV)

-continued
Process (c)

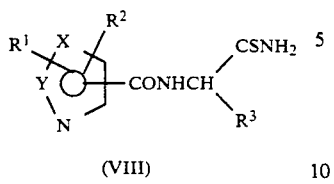

(VIII)

The thioamide derivative (VIII) can be obtained by treating the compound (IV) with gaseous hydrogen sulfide in the presence of a catalytically effective amount of a tertiary amine in an inert solvent, for example aliphatic halogenated hydrocarbons such as dichloromethane, chloroform, carbon tetrachloride and 1,4-dichloroethane, or aliphatic carboxylic acid esters such as methyl acetate, ethyl acetate, isopropyl acetate and ethyl propionate. The isolation and purification of the desired product may be easily carried out in a customary manner by recrystallization, column chromatography, etc.

Methods of synthesizing the heterocyclic 5-membered carboxylic acid (II) as the starting material used in this invention are described below by citing references.

(1) Thiazole-4-carboxylic acids (Journal of Chemical Society, 1946, page 87)

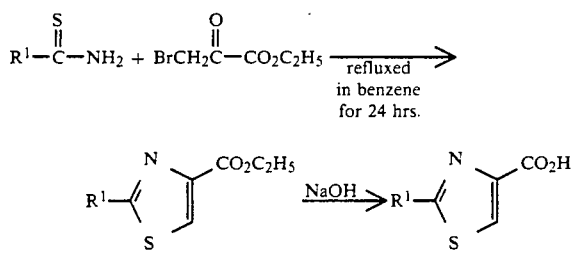

(2) Thiazole-5-carboxylic acids (Chemical Abstracts, vol. 40, page 4056)

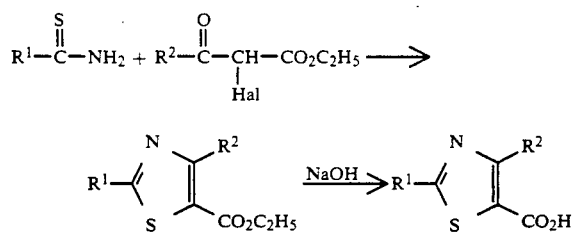

This is the so-called Hantzsch reaction.
Isothiazolecarboxylic acids (Journal of Chemical Society, 1959, page 3061)

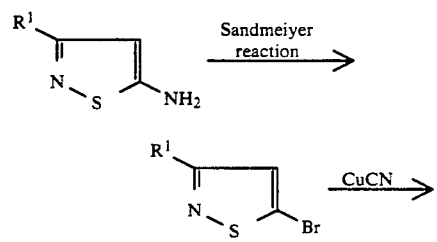

-continued

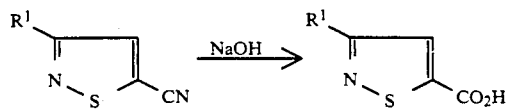

(4) 2-Halogenothiazole-5-carboxylic acids (Journal of Heterocyclic Chemistry, vol. 22, page 1621, 1985)

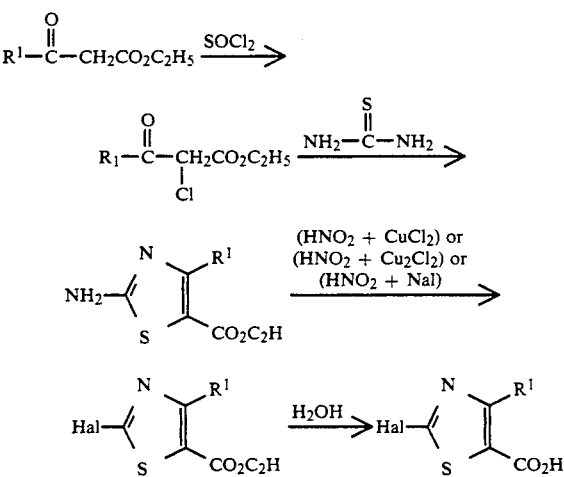

The aminoacetonitrile (III) can be easily obtained by the so-called Strecker reaction shown below.

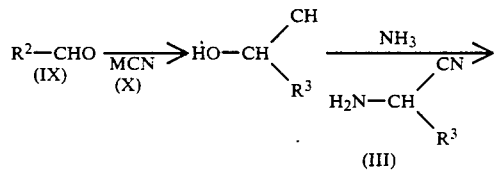

(In the above scheme, Hal represents a halogen atom.)

Specifically, it can be obtained easily by reacting an aldehyde of general formula (IX) with hydrogen cyanide [(X), M=H] or an alkali metal cyanide [(X), M=alkali metal] and ammonia or ammonium chloride in water or in a two-layer system composed of water and an organic solvent. The sequence of adding the aldehyde (IX), the cyanide (X) and ammonia or ammonium chloride is arbitrary. In any case, this reaction proceeds more efficiently in the presence of a phase transfer catalyst. The resulting aminoacetonitrile is desirably submitted to the next step immediately because it is unstable. If, however, it is converted to a mineral acid salt, it becomes a stable solid and can be stored for a long period of time.

The present invention further provides an agricultural-horticultural fungicide comprising a diluent or a carrier and/or an adjuvant, and as an active ingredient, an effective amount of at least one amide derivative represented by the following general formula (I)

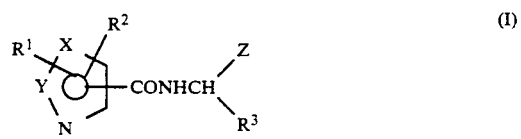

wherein one of X and Y represents a sulfur atom and the other represents a carbon atom, Z represents a nitrile or thioamide group, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group, or an unsubstituted or halo-substituted phenyl group.

When the compound of this invention is to be used as an agricultural-horticultural fungicide, it shows an excellent control effect against a broad range of plant diseases. It is especially effective against late blight and downy mildew of various crops caused by Oomycetes. The main diseases to be controlled are potato late blight (Phytophthora infestans), tomato late blight (Phytophthora infestans), tobacco black shank (Phytophthora nicotiana var. nicotiana), strawberry red stele (Phytophthora sp.), stem and root rot of soybean (Phytophthora megasperma var. sojae), grape downy mildew (Plasmopara viticola), cucumber downy mildew (Pseudoperonospora cubensis), hop downy mildew (Pseudoperonospora humuli), spinach downy mildew (Peronospora spinaciae), and dampingoff or seedling blight of various crops caused by aphanomyces, Pythium, etc. Another great charactristic of the amide derivatives of the invention is that when applied to crops, they hardly show phytotoxicity which is seen with other amide dervatives.

The compound of the invention is applied for example by seed dressing, foliar spray, soil treatment, etc. The compound of the invention exhibits a sufficient efficacy when applied by methods which those skilled in the art usually employ. The rate of application of the compound of the invention and the concentration in which it is applied may vary depending upon the crop and disease to be treated, the degree of occurrence of the disease, the formulation of the compound, the method of application and various environmetal conditions. When it is sprayed, the suitable amount of the compound as an active ingredient is 50 to 5,000 g/ha, preferably 100 to 2,000 g/ha. When the formulation as a wettable powder or emulsifiable concentrate is diluted with water and sprayed, the ratio of dilution is preferably 200 to 10,000, preferaly 500 to 5,000.

The agricultural-horticultural fungicidal composition of this invention may be used or formulated together with another agricultural chemical such as another fungicide, an insecticide or a plant growth regulator, a soil conditioner, or a fertilizing substance.

The compound of this invention may be applied as such, but preferably in the form of a composition with a carrier (meant to include a solid or liquid diluent as well). The carrier, as used herein, means a synthetic or natural inorganic or organic substance which is incorporated in order to aid in the arrival of the active ingredient at a site to be treated and make it easy to store, transport and handle the compound as the active ingredient.

Suitable solid carriers include, for example, clays such as montmorillonite and kaolinite, inorganic substances such as diatomaceous earth, terra alba, talc, vermiculite, gypsum, calcium carbonate, silica gel and ammonium sulfate, vegetable organic substances such as soybean meal, sawdust and wheat flour, and urea.

Suitable liquid carriers include, for example, aromatic hydrocarbons such as toluene, xylene and cumene, paraffinic hydrocarbons such as kerosene and mineral oils, halogenated hydrocarbons such as carbon tetrachloride, chloroform and dichloroethane, ketones such as acetone and methyl ethyl keone, ethers such as dioxane and tetrahydrofuran, alcohols such as methanol, ethanol, propanol and ethylene glycol, dimethylformamide, dimethyl sulfoxide, and water.

To enhance the efficacy of the compound of the invention, adjuvants to be described below may be used singly or in combination depending upon the type of the formulation, the situation of application, etc.

For purposes of emulsification, dispersion, spreading, wetting, binding and stabilization, there may be used, for example, anionic surface-active agents such as ligninsulfonates, alkylbenzenesulfonates, alkylsulfuric ester salts, polyoxyalkylenealylsulfates and polyoxyalkylenealkylphosphoric ester salts; nonionic surface-active agents such as polyoxyalkylene alkyl ethers, polyoxyalkylene alkylaryl ethers, polyoxyalkylene alkylamines, polyoxyalkylene alkylamides, polyoxyalkylene alkyl thioethers, polyoxyalkylene fatty acid esters, glycerin fatty acid esters, sorbitan fatty acid esters, polyoxyalkylene sorbitan fatty acid esters and polyoxypropylene/polyoxyethylene block polymers; lubricants such as calcium stearate and waxes; stabilizers such as isopropyl hydrogen phosphate and methyl cellulose, carboxy methyl cellulose, casein and gum arabic. These components should not be limited to the specific examples given above.

Usually, the amount of the active ingredient in the composition of this invention is 0.5 to 20% by weight for a dust, 5 to 20% by weight for an emulsifiable concentrate, 10 to 90% by weight for a wettable powder, 0.1 to 20% by weight for granules, and 10 to 90% by weight for a flowable agent. The amount of the carrier in the formulation is usually 50 to 99% by weight for a dust, 60 to 95% for an emulsifiable concentrate, 10 to 90% by weight for a wettable powder, 80 to 99% by weight for granules and 10 to 90% for a flowable agent. The amount of the adjuvant is usually 0.1 to 20% by weight for a dust, 1 to 20% by weight for an emulsifiable concentrate, 0.1 to 20% by weight for a wettable powder, 0.1 to 20% by weight for granules, and 0.1 to 20% by weight for a flowable agent.

The present invention also provides an agricultural-horticultural fungicidal composition comprising a diluent or a carrier and/or an adjuvant, and as a first active ingredient at least one amide derivative represented by the following general formula (I)

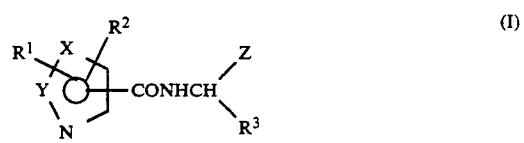

(I)

wherein one of X and Y represents a sulfur atom and the other represents a carbon atom, Z represents a nitrile or thioamide group, each of $R^1$ and $R^2$ represents a hydrogen atom, a halogen atom, an alkyl group having 1 to 6 carbon atoms, a halomethyl group or a phenyl group, and $R^3$ represents an alkenyl group having 2 to 6 carbon atoms, a haloalkenyl group having 2 to 4 carbon atoms, a furyl group, a thienyl group, an alkoxy group having 1 to 4 carbon atoms, an alkylthio group having 1 to 4 carbon atoms, an alkynyloxy group having 3 to 5 carbon atoms, an alkynylthio group having 3 to 5 carbon atoms, a pyrazolyl group, or an unsubstituted or halo-substituted phenyl group
and as a second active ingredient at least one of acylalanine fungicides having the action of controlling plant diseases caused by Oomycetes, dithiocarbamate fungicides, N-haloalkylthioimide fungicides, inorganic copper fungicides, tetrachloroisophthalonitrile, dichlofluanide and fluazinam.

As the second active component used in this composition, examples of the acylalanine fungicides are metalaxyl, furalaxyl, benalaxyl, ofurace, oxadixyl and cyprofuram. Examples of the dithiocarbamate fungicides are zineb, maneb, mancozeb, polycarbomate and propineb. Captan, captafol and folpet are examples of the N-halo-alkylthioimide fungicides. Examples of the inorganic copper fungicides are cupric sulfate, basic cupric sulfate, basic cupric chloride and cupric hydroxide.

The above compound of this invention has both a preventive and a curative effect against a broad range of diseases in fruit trees and vegetables, and shows an excellent control effect against those plant diseases of which pathogenic fungi have acquired resistance to conventional fungicidal chemicals. Furthermore the composition of this invention shows a sufficiently long residual effect and does not show phytotoxicity. It also has extremely low toxicity to warm-blooded animals and fish.

As an agricultural-horticultural fungicide, the composition of this invention shows a control effect against a wide range of plant diseases. Examples of plant diseases against which the composition of the invention shows an excellent control effect include ripe rot (*Glomerella cingulata*), anthracnose (*Elsinoe ampelina*), powdery mildew (*Uncinula necator*), rust (Phacospora ampelopsidis) and downy mildew (Plasmopara viticola) of grape; rust (*Gymnosporangium yamadae*), Alternaria leaf spot (*Alternaria mali*), fruit spot (*Mycosphaerella pomi*), scab (*Venturia inaequalis*) and powdery mildew (*Podosphaera leucotricha*) of apple; anthracnose (*Colletotrichum lagenarium*), powdery mildew (*Sphaerotheca fuliginea*), gummy stem blight (*Mycosphaerella melonis*), downy mildew (*Pseudoperonospora cubensis*), Phytophthora rot (*Phytophthora melonis*), scab (*Cladosporium cucumerinum*) and bacterial spot (*Pseudomonas lachrymans*) of cucuribit; early blight (*Alternaria solani*), leaf mold (Cladosporium fulvum), Phytophthora rot (*Phtophthora capsici*), late blight (*Phytophthora infestans*) and powdery mildew (*Erysiphe cichoracearum*) of tomato; Alternaria leaf spot (*alternaria japonica*), white spot (*Cercosporella brassicae*) and downy mildew of cruciter; rust (*Puccinia alli*) and downy mildew (*Peronospora destructor*) of green onion; downy mildew (*Peronospora spinaciae*) of spinach; scab (*Elsinoe glycines*), purple speck (*Cercospora kikuchii*) and downy mildew (*Peronosporamanshurica*) of soybean; anthracnose (Colletotrichum Iindemuthianum) and rust (*Uromnyces appendiculatus*) of kidneybean; downy mildew (*Peronospora viciae*) of field beans; black shank (*Phytophthora nicotiana var. nicotiana*) of tobacco; early blight (*Alternaria solani*) and late blight (*Phytophthora infestans*) of potato; downy mildew (*Pseudoperonospora humuli*) of hop; Phytophthora rot (*Phytophthora cinnamomi*) of pineapple; Phytophthora blight of green pepper (*Phytophthora capsici*); powdery mildew (*Sphaerotheca humuli*) and red stele (Phytophthora fragarie) of strawberry; and grey mold (Botrytis cinerea), sclerotinis disease (Sclerotinia sclerotiorum) and damping-off (by Phythium, etc.) of various crops.

The compound of the invention is applied for example by seed dressing, foliar spray, soil treatment, etc. The compound of the invention exhibits a sufficient efficacy when applied by methods which those skilled in the art usually employ. The rate of application of the compound of the invention and the concentration in which it is applied may vary depending upon the crop and disease to be treated, the degree of occurrence of the disease, the formulation of the compound, the method of application and various environmental conditions. When it is to be sprayed, the suitable amount of the compound as an active ingredient is 50 to 5,000 g/ha, preferably 100 to 2,000 g/ha. When it is to be sprayed as a wettable powder or emulsifiable concentrate diluted with water, the ratio of dilution is preferably 200 to 10,000, preferably 500 to 5,000.

The agricultural-horticultural fungicidal composition of this invention may be used, or formulated, together with another agricultural chemical such as another fungicide, an insecticide or a plant growth regulator, a soil conditioner, or a fertilizing substance.

The compound of this invention may be applied as such, but preferably in the form of a composition with a carrier (meant to include a solid or liquid diluent as well). The carrier, as used herein, means a synthetic or natural inorganic or organic substance which is incorporated in order to aid in the arrival of the active ingredients at a site to be treated and make it easy to store, transport and handle the compound as the active ingredients.

Suitable solid carriers and liquid carriers and adjuvants may be the same as those exemplified above.

Usually, the amount of the active ingredients in the composition of this invention is 0.5 to 20% by weight for a dust, 5 to 20% by weight for an emulsifiable concentrate, 10 to 90% by weight for a wettable powder, 0.1 to 20% by weight for granules, and 10 to 90% by weight for a flowable agent. The amount of the carrier in the formulation is usually 50 to 99% by weight for a dust, 60 to 95% by weight for an emulsifiable concentrate, 10 to 90% by weight for a wettable powder, 80 to 99% by weight for granules and 10 to 90% by weight for a flowable agent. The amount of the adjuvant is usually 0.1 to 20% by weight for a dust, 1 to 20% by weight for an emulsifiable concentrate, 0.1 to 20% by weight for a wettable powder, 0.1 to 20% by weight for granules, and 0.1 to 20% by weight for a flowable agent. The ratio of the fungicide as the second active ingredient to the amide derivative of the invention can be freely changed between 0.1 and 30.

The processes for producing the amide derivatives of general formula (I) provided by this invention will be specifically illustrated by the following Synthesis Examples.

SYNTHESIS EXAMPLE 1

Synthesis of N-(alpha-cyanofurfuryl)-2-chloro4-methylthiazole-5-carboxy amide (compound No. 37).

8.8 g of 2-chloro-4-methylthiazole-5-carboxylic acid was suspended in 7 ml of thionyl chloride, and one drop of N,N-dimethylformamide was added. The mixture was heated under reflux for 1 hour, and then the excess of thionyl chloride was evaporated under reduced pressure. Benzene (10 ml) was added, and the mixture was evaporated under reduced pressure. This procedure was repeated three times to give 9.7 g of 2-chloro-4-methylthiazole-5-carboxylic acid chloride which was used in the following reaction without purification.

The 2-chloro-4-methylthiazole-5-carboxylic acid chloride (1.6 g) was suspended in 30 ml of pyridine, and 1.3 g of alpha-2-furyl)-alpha-aminoacetonitrile hydrochloride was added. The mixture was stirred at room temperature for 2 hours. After the reaction, the reaction mixture was filtrated. The filtrate was concentrated, and the residue was purified by silica gel column chromatography. Elution with hexane ethyl acetate gave 1.79 g (yield 75.2%) of the desired N-(alpha-cyanofurfuryl) -2-chloro-4-methylthiazole-5-carboxylic acid amide.

SYNTHESIS EXAMPLE 2

Synthesis of N-(alpha-cyanofurfuryl)-2,4-dimethylthiazole-5-carboxylic acid amide (compound No. 2).

9.30 g of 2,4-dimethylthiazole-5-carboxylic acid was suspended in 90 ml of toluene, and 15.0 g of phosphorus pentachloride was added. The mixture was refluxed for 1 hour. Under reduced pressure, the resulting phosphorus oxychloride and the toluene were evaporated to give 2,4-dimethylthiazole-5-carboxylic acid chloride which was used in the following reaction without purification.

In 120 ml of ethylacetate were dissolved 6.2 g of alpha-(2-furyl)-alpha-aminoacetonitrile and 6.0 g of triethylamine, and with stirring, the 2,4-dimethylthiazole5-carboxylic acid chloride was added dropwise to the solution, and the mixture was stirred at room temperature for 1 hour. Water (150 ml) was added, and the precipitated triethylamine hydrochloride was dissolved. The ethyl acetate layer was separated, washed with water, and dried over sodium sulfate. The dried ethyl acetate layer was distilled under reduced pressure to remove the solvent. The residue was recrystallized from isopropyl ether to give 11.65 g (yield 90.0%) of the desired N-(alpha-cyanofurfuryl)-2,4-dimethylthiazole-5-carboxylic acid amide.

SYNTHESIS EXAMPLE 3

Synthesis of N-(alpha-cyanofurfuryl)-2,4-diethylthiazole-5-carboxylic acid amide (compound No. 12).

In accordance with the method of Synthesis Example 2, 2,4-diethylthiazole-5-carboxylic acid and phosphorus pentachloride were reacted to give 2,4-diethylthiazole-5-carboxylic acid chloride quantitatively. The 2,4-diethylthiazole-5-carboxylic acid chloride was used in the following reaction without purification.

2.80 g of alpha-(2-furyl)-alpha-aminoacetonitrile and 6.0 g of triethylamine were dissolved in 50 ml of ethyl acetate, and with stirring, 2.1 g of the 2,4-diethylthiazole-5-carboxylic acid chloride was added dropwise, and the mixture was stirred at room temperature for 1 hour. Water (150 ml) was added, and the precipitated triethylamine hydrochloride was dissolved. The ethyl acetate layer was separated, washed with water and dried over sodium sulfate. The dried ethyl acetate layer was evaporated under reduced pressure to remove the solvent. The residue was recrystallized from n-hexane to give 2.41 g (yield 80.0%) of the desired N-(alphacyanofurfuryl)-2,4-dimethylthiazole-5-carboxylic acid amide.

SYNTHESIS EXAMPLE 4

Synthesis of N-(alpha-cyanofurfuryl)-2,4-dimethylthiazole-5-carboxylic acid amide (compound No. 2) by using a mixed acid anhydride.

4.71 g of 2,4-dimethylthiazole-5-carboxylic acid was suspended in 70 ml of tetrahydrofuran, and 6.67 g of triethylamine was added. The mixture was stirred. While it was cooled to $-10°$ to $-5°$ C., 4.10 g of n-butyl chloroformate was added, and the mixture was stirred at this temperature for 30 minutes, and then 4.03 g of alpha-(2-furyl)-alpha-aminoacetonitrile hydrochloride was added. The mixture was stirred at room temperature for 5 hours, and then left to stand overnight. The precipitate was separated by filtration and distilled under reduced pressure to remove the solvent. The residue was purified by silica gel column chromatography. Elution with hexane/ethyl acetate gave 4.20 g (yield 53.6%) of the desired N-(alpha-cyanofurfuryl)-2,4-dimethylthiazole-5-carboxylic acid amide.

SYNTHESIS EXAMPLE 5

Synthesis of N-(alpha-cyanofurfuryl)-2,4-dimethylthiazole-5-carboxylic acid amide (compound No. 2) by the CDI method.

4.0 g of alpha-(2-furyl)-alpha-aminoacetonitrile hydrochloride and a mixture of 3.70 g of a 50% aqueous soution of NaOH and 50 ml of isopropyl ether were stirred at 40° C. for 1 hour under a nitrogen gas. The isopropyl ether layer was separated. Separately, while 4.71 g of 2,4-dimethylthiazole-5-carboxylic acid and 4.88 g of carbonyldiimidazole (CDI) were stirred in 50 ml of methylene chloride, the alpha-(2-furyl)-alpha-aminoacetonitrile in isopropyl ether was added dropwise under ice cooling. The mixture was left to stand overnight at room temperature, and distilled under reduced pressure to remove the solvent. The residue was dissolved in ethyl acetate, separated, washed with water, and dried over sodium sulfate. The ethyl acetate layer was distilled under reduced pressure to remove the solvent. The residue was recrystallized from isopropyl ether to give 5.51 g (yield 70.4%) of the desired N-(alpha-cyanofurfuryl)-2,4-dimethylthiazole-5-carboxylic acid amide.

SYNTHESIS EXAMPLE 6

Synthesis of N-(alpha-cyanofurfuryl)-2,4-dimethylthiazole-5-carboxylic acid amide (compound No. 2) by the DCC method.

3.0 g of alpha-(2-furyl)-alpha-aminoacetonitrile hydrochloride and a mixture of 70 g of a 50% aqueous solution of NaOH and 30 ml of methylene chloride were stirred at 40° C. for 1 hour under a nitrogen gas. Then, the methylene chloride layer was separated. Separately, while 2.50 g of 2,4-dimethylthiazole-5-carboxylic acid and 3.10 g of dicyclohexylcarbodiimide (DCC) were stirred in 50 ml of methylene chloride, the alpha-(2-furyl)-alpha-aminoacetonitrile was added dropwise under cooling with ice water over the course of 1 hour. After the addition, the mixture was stirred for 1 hour under ice cooling, left to stand overnight at room temperature, and distilled under reduced pressure to remove the solvent. The residue was dissolved in ethyl acetate, separated, washed with water and dried over sodium sulfate. The ethyl acetate layer was distilled under reduced pressure to remove the solvent. The residue was purified by silica gel column chromatography. Elution with hexane/ethyl acetate gave 1.85 g (yield 47.3%) of the desired N-(alpha-cyanofurfuryl)-2,4-dimethylthiazole-5-carboxylic acid amide.

SYNTHESIS EXAMPLE 7

Synthesis of N-(alpha-cyanofurfuryl)-3-methylisothiazole-4-carboxylic acid amide (compound No. 32).

1.2 g of alpha-(2-furyl)-alpha-aminoacetonitrile hydrochloride was dissolved in 10 ml of pyridine, and with stirring at room temperature, 1.1 g of 3-methylisothiazole-4-carboxylic acid chloride was added dropwise. After the dropwise addition, the mixture was stirred for 1 hour, and distilled under reduced pressure to remove pyridine. The residue was dissolved in ethyl acetate, separated, washed with water, and dried over sodium sulfate. The ethyl acetate layer was distilled under reduced pressure to remove the solvent. The residue was purified by silica gel column chromatography. Elution with benzene-ethyl acetate gave 1.2 g (yield 70%) of the desired N-(alpha-cyanofurfuryl)-3-methylisothiazole-4-carboxylic acid amide

SYNTHESIS EXAMPLE 8

Synthesis of N-(alpha-cyanofurfuryl)-3-methylisothiazole-5-carboxylic acid amide (compound No. 34).

5.0 g of alpha-(2-furyl)-alpha-aminoacetonitrile hydrochloride was dehydrochlorinated with sodium hydroxide in ethyl acetate by the same method as in the above Synthesis Example 6. Pyridine (2.5 g) was added, and furthermore, an ethyl acetate solution of 4.0 g of 3-methylisothiazole-5-carboxylic acid chloride was added dropwise After the addition, the mixture was stirred for 1 hour. The reaction mixture was washed with water, dilute hydrochloric acid and a dilute aqueous solution of sodium bicarbonate. Sodium sulfate, and active carbon were added to dehydrate and decolorize the reaction mixture. The solvent was removed under reduced pressure, and the residue was washed with ethyl ether to give 4.5 g (yield 74%) of the desired N-(alpha-cyanofurfuryl)-3-methylisothiazole-5-carboxylic acid amide

SYNTHESIS EXAMPLE 9

Synthesis of N-(1-cyano-3-methyl-2-butenyl)3-methylisothiazole-5-carboxylic acid amide (compound No. 36).

To a mixture of 30 ml of water and 30 ml of ethyl ether were added 3 ml of 28% aqueous ammonia, 2.0 g of sodium cyanide, 4.5 g of ammonium chloride and 0.5 g of triethyl benzyl ammonium chloride, and the mixture was cooled to 5° C. With stirring a solution of 2.8 g of 3-methyl-2-butenal was added dropwise After the dropwise addition, the mixture was continuously stirred at 15 to 20° C. for 5 hours The ether layer was separated, washed with water and dried over sodium sulfate to give an ether solution of 1-cyano-3-methyl-2-butenylamine. Triethylamine (1.0 g) was added to the solution, and with stirring at room temperature, an ethyl acetate solution of 1.1 g of 3-methylisothiazole-5-carboxylic acid chloride was added dropwise After the addition, the mixture was stirred for 1 hour, washed with water, and distilled under reduced pressure to remove the solvent. The residue was purified by silica gel column chromatography. Elution with benzene/ethyl acetate gave 1.0 g (yield 63%) of the desired N-(1-cyano-3-methyl-2-butenyl)-3-methylisothiazole-5-carboxylic acid amide.

SYNTHESIS EXAMPLE 10

Synthesis of N-(alpha-cyanobenzyl)-2-methylisothiazole-5-carboxylic acid amide (compound No. 35).

1.2 g of alpha-benzyl-alpha-aminoacetonitrile hydrochloride was suspended in 20 ml of ethyl acetate, and 7 ml of 10% NaOH was added dropwise at a temperature below 10° C. The mixture was stirred at this temperature for 10 minutes, and an ethyl acetate solution of 0.8 g of 3-methylisothiazole-5-carboxylic acid chloride was added dropwise at 0° C. After the addition, the mixture was stirred for 30 minutes. The ethyl acetate layer was washed with water, and distilled under reduced pressure to remove the solvent. The residue was purified by silica gel column chromatography. Elution with benzene/ethyl acetate gave 1.0 g (yield 77%) of the desired N-(alpha-cyanobenzyl)-3-methylisothiazole-5-carboxylic acid amide.

SYNTHESIS EXAMPLE 11

Synthesis of N-[alpha-cyano-alpha-(1-pyrazolyl)methyl]-3-methylisothiazole-5-carboxylic acid amide (compound No. 46).

0.7 g of N-(cyanomethyl)-3-methylisothiazole5-carboxylic acid amide was dissolved in 30 m 1 of ethyl acetate. Bromine (0.8 g) was added and the mixture was stirred for 30 minutes, and then cooled over an ice bath. A mixture of 0.3 g of pyrazole, 1.0 g of triethylamine and 5 ml of ethyl acetate was added to the reaction mixture with stirring. The mixture was stirred for 30 minutes. The ethyl acetate layer was washed with water and distilled under reduced pressure to remove the solvent. The residue was purified by silica gel column chromatography. Elution with benzene/ethyl acetate gave 0.75 g (yield 78%) of the desired N-[alpha-cyano-alpha(1-pyrazolyl)methyl]-3-methylisothiazole-5-carboxylic acid amide.

SYNTHESIS EXAMPLE 12

Synthesis of N-[alpha-cyano-alpha-(1-pyrazolyl)methyl]-2,4-dimethylthiazole-5-carboxylic acid amide (compound No. 38).

(1) Synthesis of N-cyanomethyl-2,4-dimethylthiazole-5-carboxylic acid amide;

A mixture of 10 g of 2,4-dimethylthiazole-5-carboxylic acid, 13.6 g of thionyl chloride and 70 ml of toluene was cooled with ice, and with stirring, 8.4 g of N,N-dimethylformamide was added. The mixture was stirred for 3 hours at 3° to 5° C. and then for 1 hour at 20° C., and 200 ml of toluene and 37 g of triethylamine were added. An ethyl acetate solution of aminoacetonitrile prepared from aminoacetonitrile sulfate using ethyl acetate and NaOH was gradually added to the reaction mixture being cooled with ice. The mixture was stirred at room temperature for 1 hour. The reaction mixture was poured into water and extracted with ethyl acetate.

The ethyl acetate layer was washed with water, dried, and distilled under reduced pressure to remove the solvent. The residue was purified by silica gel column chromatography. Elution with hexane/ethyl acetate gave 6.6 g (yield 53%) of N-cyanomethyl-2,4-diethyl-thiazole-5-carboxylic acid amide.

(2) Synthesis of
N-[alpha-cyano-alpha-(1-pyrazolyl)methyl]-2,4-dimethylthiazole-5-carboxylic acid amide.

1.0 g of N-cyanomethyl-2,4-dimethylthiazole5-carboxylic acid amide was dissolved in 30 ml of ethyl acetate. Bromine (0.3 ml) was added and the mixture was refluxed until the dark brown color of bromine disappeared. The reaction mixture was cooled over an ice bath, and 0.5 g of pyrazole, 2.0 g of triethylamine and 10 ml of ethyl acetate were added at the above temperature. The mixture was stirred at room temperature for 2 hours. The reaction mixture was poured into water, and extracted with ethyl acetate. The ethyl acetate layer was washed with water, dried and distilled under reduced pressure to remove the solvent. The residue was purified by silica gel column chromatography. Elution with hexane/ethyl acetate gave 0.74 g (yield 54.9%) of the desired N-[alpha-cyano-alpha-(1-pyrazolyl)methyl]-2,4-dimethylthiazole-5-carboxylic acid amide.

SYNTHESIS EXAMPLE 13

Synthesis of
N-(alpha-cyano-alpha-ethoxymethyl)-2,4-dimethyl-thiazole-5-carboxylic acid amide 1.0 g of N-cyanomethyl-2,4-dimethylthiazole-5-carboxylic acid amide was dissolved in 30 ml of ethyl acetate. Bromine (0.3 ml) was added and the mixture was heated under reflux until the dark brown color of bromine disappeared. The reaction mixture was cooled over an ice bath, and 1.0 g of ethanol, 2.0 g of triethylamine and 10 ml of ethyl acetate were added at the above temperature. The mixture was stirred at room temperature for 2 hours. The reaction mixture was poured into water and extracted with ethyl acetate. The ethyl acetate layer was washed with water, dried, and distilled under reduced pressure to remove the solvent. The residue was purified by silica gel column chromatography. Elution with hexane/ethyl acetate gave 0.53 g (yield 43.1%) of the desired N-(alpha- cyano-alpha-ethoxymethyl)-2,4-dimethylthiazole5-carboxylic acid amide.

SYNTHESIS EXAMPLE 14

Synthesis of
N-[(alpha-thiocarbamoyl)furfuryl]-3-methylisothiazole-5-carboxylic acid amide (compound No. 47).

1.0 g of N-(alpha-cyanofurfuryl)-3-methylisothiazole-5-carboxylic acid amide was dissolved in 30 ml of tetrahydrofuran, and 0.6 ml of triethylamine was added. With stirring at room temperature, hydrogen sulfide gas was introduced into the mixture. Five hours later, the reaction solvent was evaporated under reduced pressure. Water was added to the residue. The precipitated crystals were separated by filtration to give 1.1 g of the desired N-[(alpha-thiocarbamoyl)furfuryl]-3-methylisothiazole-5-carboxylic acid amide.

Table 1 below shows typical examples of the amide derivatives of general formula (I) provided by this invention. The designations (a), (b) and (c) in the column of "Process" means the processes (a), (b) and (c), respectively, described above.

TABLE 1

| Compound No. (process) | Substituent $R^1, R^2, X, Y$ (ring) | $R^3$ | Z | m.p. (°C.) | NMR(100 MHz, δ) |
|---|---|---|---|---|---|
| 1 (a) | 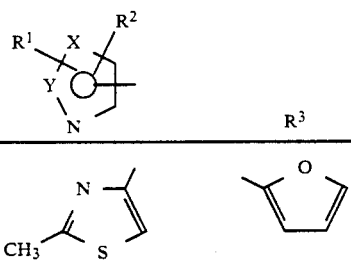 | 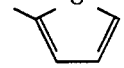 | CN | oil | (CDCl₃)2.72(3H, s), 6.24–6.66(3H, m), 7.34–7.49(1H, m), 7.97(1H, broad d, J=7Hz), 8.04(1H, s) |
| 2 (a) | 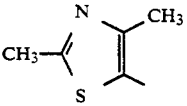 | " | " | 100.5–101.5 | (CDCl₃)2.61(3H, s), 2.64(3H, s), 6.34 (1H, d, J=8.0Hz), 6.40(1H, m), 6.58(1H, m), 7.48(1H, m), 7.96(1H, d, J=8.0Hz) |
| 3 (a) | " | 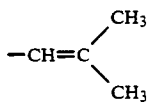 | " | 99–100 | (CDCl₃)1.84(6H, s), 2.71(6H, s), 5.34(1H, d, J=8.0Hz), 5.68(1H, t, J=8.0Hz), 6.16 (1H, d, J=8.0Hz) |
| 4 (a) | " |  | " | 115.5–118.5 | (CDCl₃)2.66(6H, s), 6.42(1H, d, J=9.0Hz), 6.98(2H, m), 7.34(1H, d, J=8.0Hz), 7.38 (1H, d, J=9.0Hz) |
| 5 (a) | " | 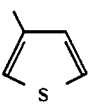 | " | 90–93 | (CDCl₃)2.60(6H, s), 6.18(1H, d, J=9.0Hz), 6.68(1H, d, J=9.0Hz), 7.0–7.1(1H, m), 7.28–7.44 (2H, m) |

TABLE 1-continued

| Compound No. (process) | Substituent (R¹-X, R²/Y-N ring) | R³ | Z | m.p. (°C.) | NMR(100 MHz, δ) |
|---|---|---|---|---|---|
| 6 (a) | " | phenyl | " | 132-135 | (CDCl₃)2.61(6H, s), 6.18(1H, d, J=9.0Hz), 6.81(1H, d, J=9.0Hz), 7.28-7.52(5H, m) |
| 7 (a) | N=CH, S, CH₃, (methyl) | furan (O) | CN | oil | (CDCl₃)2.72(3H, s), 6.26(1H, d, J=8.0Hz), 6.36(1H, m), 6.54(1H, broad d, J=4Hz), 6.95(1H, d, J=8.0Hz), 7.43(1H, broad d, J=4Hz), 8.65(1H, s) |
| 8 (a) | " | phenyl | " | oil | (CDCl₃)2.62(3H, s), 6.16(1H, d J=8.0Hz), 7.2-7.5(5H, m), 8.46(1H, s) |
| 9 (a) | C₂H₅-C(S)=N, CH₃ | furan (O) | " | 99-102 | (CDCl₃)1.40(3H, t, J=8Hz), 2.70(3H, s), 3.00(2H, q, J=8Hz), 6.36(1H, broad d, J=8Hz), 6.4-6.7(2H, m), 6.78(1H, broad d, J=8Hz), 7.42(1H, m) |
| 10 (a) | " | thiophene (S) | " | 90.5-91.6 | (CDCl₃)1.34(3H, t, J=7Hz), 2.68(3H, s), 2.98(2H, q, J=7Hz), 6.41(1H, d, J=8Hz), 6.61(1H, broad d, J=8Hz), 6.96-7.12(1H, m), 7.23-7.48(2H, m) |
| 11 (a) | " | phenyl | " | oil | (CDCl₃)1.36(3H, t, J=7Hz), 2.66(3H, s), 2.96(2H, q, J=7Hz), 6.22(1H, d, J=8Hz), 6.46(1H, broad d, J=8Hz), 7.12-7.60(5H, m) |
| 12 (a) | C₂H₅-C(S)=N, C₂H₅ | furan (O) | " | 114.5-115.5 | (CDCl₃)1.30(3H, t, J=8Hz), 1.38(3H, t, J=8Hz), 2.98(2H, q, J=8Hz), 3.09(2H, q, J=8Hz), 6.28(1H, d, J=8Hz), 6.40(1H, m), 6.56(2H, m), 7.48(1H, m) |
| 13 (a) | " | thiophene (S) | " | 117-118 | (CDCl₃)1.31(3H, t, J=8Hz), 1.39(3H, t, J=8Hz), 2.97(2H, q, J=8Hz), 3.05(2H, q, J=8Hz), 6.29(1H, d, J=9Hz), 6.74(1H, broad d, J=9Hz), 7.00(1H, m), 7.2-7.4(2H, m) |
| 14 (a) | C₂H₅-C(S)=N, C₂H₅ | phenyl | CN | 79-81 | (CDCl₃)1.26(3H, t, J=8Hz), 1.34(3H, t, J=8Hz), 2.92(2H, q, J=8Hz), 3.00(2H, q, J=8Hz), 6.21(1H, d, J=9Hz), 6.67(1H, d, J=9Hz), 7.20-7.50(5H, broad s) |
| 15 (a) | n-C₃H₇-C(S)=N, CH₃ | furan (O) | " | oil | (CDCl₃)1.02(3H, t, J=7Hz), 1.80(2H, m, J=7Hz), 2.68(3H, s), 2.91(2H, t, J=7Hz), 6.31(1H, d, J=8Hz), 6.42, 6.59, 7.47(each 1H, m), 6.80(1H, broad d, J=8Hz) |
| 16 (a) | " | thiophene (S) | " | oil | (CDCl₃)1.00(3H, t, J=7Hz), 1.78(2H, m, J=7Hz), 2.66(3H, s), 2.89(2H, t, J=7Hz), 6.41(1H, d, J=8Hz), 6.62(1H, broad d, J=8Hz), 7.0-7.4(3H, m) |
| 17 (a) | CH₃-C(S)=N, C₂H₅ | furan (O) | " | oil | (CDCl₃)1.30(3H, t, J=7Hz), 2.69(3H, s), 3.47(2H, q, J=7Hz), 6.29(1H, d, J=8Hz), 6.29-6.72(3H, m), 7.28-7.71(1H, m) |
| 18 (a) | " | thiophene (S) | " | 124.5-125.8 | (CDCl₃)1.20(3H, t, J=8Hz), 2.67(3H, s), 2.96(2H, q, J=8Hz), 6.53(1H, d, J=7Hz), 7.00-7.72(3H, m), 9.61(1H, broad d, J=7Hz) |

TABLE 1-continued

| Compound No. (process) | Substituent (R¹, X, R², Y, N, O) | R³ | Z | m.p. (°C.) | NMR(100 MHz, δ) |
|---|---|---|---|---|---|
| 19 (a) | " | phenyl | " | 111–112 | (CDCl₃)1.27(3H, t, J=7Hz), 2.67(3H, s), 3.03 (2H, q, J=7Hz), 6.22(1H, d, J=8Hz), 6.66(1H, broad d, J=8Hz), 7.20–7.64(5H, m) |
| 20 (a) | CH₃–C(=N)(S)–C(n-C₃H₇)=C(CH₃)– | furan-2-yl (O) | " | 117–118 | (CDCl₃)0.96(3H, t, J=8Hz), 1.74(2H, m, J=8Hz), 2.70(3H, s), 3.02(2H, t, J=8Hz), 6.32 (1H, d, J=8Hz), 6.45, 6.60, 7.70(each 1H, m), 6.88(1H, broad d, J=8Hz) |
| 21 (a) | CH₃–C(=N)(S)–C(n-C₃H₇)=C(CH₃)– | thien-2-yl (S) | CN | 117.5–119 | (CDCl₃)0.96(3H, t, J=8Hz), 1.54(2H, m, J=8Hz), 2.68(3H, s), 3.01(2H, t, J=8Hz), 6.44(1H, d, J=8Hz), 6.90–7.50(4H, m) |
| 22 (a) | " | phenyl | " | 93–94 | (CDCl₃)0.93(3H, t, J=8Hz), 1.70(2H, m, J=8Hz), 2.66(3H, s), 2.98(2H, t, J=8Hz), 6.25(1H, d, J=9Hz), 6.84(1H, broad d, J=9Hz), 7.28–7.74 (5H, m) |
| 23 (a) | CH₃–C(=N)(S)–C(CF₃)=C(CH₃)– | furan-2-yl (O) | " | 105–107 | (CDCl₃)2.77(3H, s), 6.23(1H, d, J=8Hz), 6.45 (1H, m), 6.62(1H, m), 6.93(1H, broad d, J=8Hz), 7.50(1H, m) |
| 24 (a) | " | thien-2-yl (S) | " | oil | (CDCl₃)2.76(3H, s), 6.39(1H, d, J=8Hz), 6.90–7.13(2H, m), 7.36–7.48(2H, m) |
| 25 (a) | HC(=N)(S)–C(C₂H₅)=CH– | furan-2-yl (O) | " | 98.5–99.0 | (CDCl₃)1.34(3H, t, J=8Hz), 3.20(2H, q, J=8Hz), 6.30(1H, d, J=8Hz), 6.42(1H, m), 6.60(1H, m), 6.72(1H, broad d, J=8Hz), 7.48(1H, m), 7.74 (1H, s) |
| 26 (a) | Ph–C(=N)(S)–C(CH₃)=C(CH₃)– | " | " | 147–151 | (CDCl₃)2.74(3H, s), 6.26(1H, d, J=8Hz), 6.3–6.7(4H, m), 7.3–7.5(3H, m), 7.8–7.9(2H, m) |
| 27 (a) | Ph–C(=N)(S)–C(CH₃)=C(CH₃)– | thien-2-yl (S) | CN | 162–163 | (CDCl₃)2.64(3H, s), 6.26(1H, d, J=8Hz), 6.8 (1H, m), 7.1–7.3(5H, m), 7.7(2H, m), 9.24 (1H, broad d, J=8Hz) |
| 28 (a) | " | phenyl | " | 138–139 | (CDCl₃)2.73(3H, s), 6.25(1H, d, J=8Hz), 6.66 (1H, broad d, J=8Hz), 7.36–7.62(8H, m), 7.82–7.97(2H, m) |
| 29 (a) | CH₃–C(=N)(S)–C(Ph)=C(CH₃)– | furan-2-yl (O) | " | 233.5–234.5 | (CDCl₃)2.72(3H, s), 6.40(1H, d, J=8Hz), 6.45–6.68(2H, m), 7.32–7.87(6H, m), 9.78(1H, broad d, J=8Hz) |
| 30 (a) | " | thien-2-yl (S) | " | 216.5–218.0 | (CDCl₃)2.73(3H, s), 6.51(1H, d, J=7Hz), 6.83–7.79(8H, m), 9.82(1H, broad d, J=7Hz) |

TABLE 1-continued

| Compound No. (process) | Substituent (R¹, X, R², Y, ring, N) | R³ | Z | m.p. (°C.) | NMR(100 MHz, δ) |
|---|---|---|---|---|---|
| 31 (a) | " | phenyl-CH₃ | " | 220.5–221.5 | (CDCl₃)2.70(3H, s), 6.25(1H, d, J=7Hz), 7.04–7.74(10H, m), 9.67(1H, broad d, J=7Hz) |
| 32 (a) | isothiazole with CH₃ groups (N–S, CH₃) | furan-O | " | 126–127 | (CDCl₃)2.62(3H, s), 6.26(1H, d, J=8Hz), 6.38(1H, t, J=2Hz), 6.54(1H, d, J=2Hz), 7.44(1H, d, J=2Hz), 7.50(1H, d, J=8Hz), 9.00(1H, s) |
| 33 (a) | isothiazole with CH₃ groups | —CH=C(CH₃)₂ | CN | oil | (CDCl₃)1.84(6H, s), 2.68(3H, s), 5.34(1H, d, J=8Hz), 5.70(1H, t, J=8Hz), 7.30(1H, d, J=8Hz), 9.08(1H, s) |
| 34 (a) | isothiazole with CH₃ groups | furan-O | " | 136–137 | (DMSO-d₆)2.87(1H, s,), 6.44(1H, d, J=8Hz), 6.50(1H, t, J=2Hz), 6.62(1H, d, J=2Hz), 7.74(1H, d, J=2Hz), 7.76(1H, s), 10.02(1H, d, (J=8Hz) |
| 35 (a) | " | phenyl | " | 129–131 | (DMSO-d₆)2.54(3H, s), 6.40(1H, broad), 7.4–7.7(5H, m), 7.84(1H, s), 10.0(1H, broad) |
| 36 (a) | " | —CH=C(CH₃)₂ | " | 123–125 | (DMSO-d₆)1.78(6H, d, J=2Hz), 2.48(3H, s), 5.3–5.8(2H, m), 7.74(1H, s), 9.58(1H, d, J=8Hz) |
| 37 (a) | Cl-C=N, S, CH₃ groups | furan-O | " | 90–91 | (CDCl₃)2.55(3H, s), 6.24(1H, d, J=8Hz), 6.55(2H, m), 7.52(1H, m), 8.06(1H, d, J=8Hz) |
| 38 (b) | thiazole with CH₃ groups (CH₃–S, N, CH₃) | pyrazole (—N–N=) | " | 140–141 | (CDCl₃)2.67(3H, s), 6.30–6.40(1H, m), 7.28(1H, d, J=8Hz), 7.60–7.66(1H, m), 7.72–7.80(1H, m), 8.30(1H, d, J=8Hz) |
| 39 (b) | thiazole with CH₃ groups | —OC₂H₅ | CN | 89–90 | (CDCl₃))1.30(3H, t, J=7Hz), 2.70(3H, s), 2.73(3H, s), 3.71(2H, q, J=7Hz), 6.10(1H, d, J=10Hz), 6.95(1H, d, J=10Hz) |
| 40 (b) | " | —OCH₂C≡CH | " | oil | (CDCl₃)2.25–2.59(1H, m), 2.71(6H, s), 4.31(2H, d, J=3Hz), 6.31(1H, d, J=9Hz), 7.04(1H, d, J=9Hz) |
| 41 (b) | " | —SC₂H₅ | " | oil | (CDCl₃)1.37(3H, t, J=8Hz), 2.68(3H, s), 2.70(3H, s), 2.87(2H, q, J=8Hz), 6.15(1H, d, J=9Hz), 6.96(1H, d, J=9Hz) |
| 42 (b) | " | —OC₃H₇(n) | " | oil | (CDCl₃)0.93(3H, t, J=7Hz), 1.80(2H, m, J=7Hz), 2.68(3H, s), 2.91(2H, t, J=7Hz), 6.31(1H, d, J=8Hz), 6.42, 6.59, 7.47(each 1H, m), 6.80(1H, broad d, J=8Hz) |
| 43 (b) | " | —OCH₃ | " | oil | (CDCl₃)2.66(3H, s), 2.68(3H, s), 3.38(3H, s), 5.95(1H, d, J=9Hz), 7.08(1H, d, J=9Hz) |
| 44 (b) | " | —SC₃H₇(i) | " | 105–106 | (CDCl₃)1.36(3H, d, J=6Hz), 1.39(3H, d, J=6Hz), 2.65(3H, s), 2.68(3H, s), 3.25(1H, m, J=6Hz), 6.09(1H, d, J=9Hz), 7.03(1H, broad d, J=9Hz) |

TABLE 1-continued

| Compound No. (process) | Substituent (R¹, X, R², Y, ring with N) | R³ | Z | m.p. (°C.) | NMR(100 MHz, δ) |
|---|---|---|---|---|---|
| 45 (b) | CH₃ on 3-methylisothiazole ring | pyrazol-1-yl | CN | 134–136 | (DMSO-d₆)2.56(3H, s), 6.40(1H, t, J=2Hz), 7.64 (1H, d, J=8Hz), 7.70(1H, d, J=2Hz), 7.86(1H, s), 7.94(1H, d, J=2Hz), 10.96(1H, d, J=8Hz) |
| 46 (b) | CH₃ on 3-methylisothiazole ring | " | " | 176–178 | (DMSO-d₆)2.60(3H, s), 6.40(1H, t, J=2Hz), 7.60 (1H, d, J=8Hz), 7.66(1H, d, J=2Hz), 7.96(1H, d, J=2Hz), 9.62(1H, s), 10.56(1H, d, J=8Hz) |
| 47 (c) | CH₃ on 3-methylisothiazole ring | 2-methylfuran-5-yl | −C(=S)−NH₂ | 163–167 | (DMSO-d₆)2.48(3H, s), 5.92(1H, d, J=7.5Hz), 6.34–6.52(2H, m), 7.62(1H, s), 7.87(1H, s), 9.13(1H, d, J=7.5Hz), 9.54(1H, s), 9.82(1H, s) |
| 48 (c) | 2,4,5-trimethylthiazol-type ring | " | " | 96.5–99.0 | (DMSO-d₆)2.58(3H, s), 2.63(3H, s), 5.94(1H, d, J=8.5Hz), 6.41(2H, s), 7.57(1H, s), 8.16(1H, d, J=8.5Hz), 9.60(1H, s), 9.98(1H, s) |
| 49 (a) | CH₃−C(=N−)−C(CH₂Cl)=C(CH₃)−S− (thiazoline) | furan-2-yl | CN | 129.5–130 | (CDCl₃)2.70(3H, s), 4.9(2H, s), 6.22(1H, d, J=8Hz), 6.32–6.64(2H, m), 7.08(1H bd, J=8Hz), 7.40–7.48(1H, m) |
| 50 (a) | CH₃−C(=N−)−C(i-C₃H₇)=C(CH₃)−S− | furan-2-yl | " | 118.0–119.0 | (CDCl₃)1.24(6H, d, J=7Hz), 2.63(3H, s), 3.63 (1H, qt, J=7Hz), 6.16(1H, d, J=8Hz), 6.16–6.68 (2H, m), 6.55(1H, bd, J=8Hz), 7.16–7.39(1H, m) |
| 51 (a) | CH₃−C(=N−)−C(i-C₃H₇)=C(CH₃)−S− | thien-2-yl | CN | oil | (CDCl₃)1.28(6H, d, J=7Hz), 2.64(3H, s), 3.72 1H, qt, J=7Hz), 6.33(1H, d, J=8Hz), 6.60(1H, bd, J=8Hz), 6.75–7.22(3H, m) |
| 52 (a) | CH₃−C(=N−)−C(i-C₃H₇)=C(CH₃)−S− | phenyl | " | 95.0–98.0 | (CDCl₃)1.21(6H, d, J=7Hz), 2.57(3H, s), 3.61 (1H, qt, J=Hz), 6.08(1H d, J=8Hz), 6.61(1H, bd, J=8Hz), 7.10–7.24(5H, m) |
| 53 (a) | CH₃−C(=N−)−CH=C(CH₃)−S− | furan-2-yl | " | oil | (CDl₃)2.68(3H, s), 6.23(1H, d, J=8Hz), 6.12–6.62(2H, m), 7.20–7.44(1H, m), 7.90(1H, bd), 8.01(1H, s) |
| 54 (a) | CH₃−C(=N−)−C(C₂H₅)=C(CH₃)−S− | −CH=C(CH₃)₂ | " | 90.5–92.0 | (CDCl₃)1.27(3H, t, J=8Hz), 1.81(6H, s), 2.65 (3H, s), 3.01(2H, q, J=8Hz), 5.47(1H, d, J=8Hz), 5.60(1H bd, J=8Hz), 6.48(1H, bd, J=8Hz) |
| 55 (a) | " | 2-chlorophenyl | " | 113–116 | (CDCl₃)1.32(3H, t, J=8Hz), 2.75(3H, s), 3.11 (2H, q, J=8Hz), 6.58(1H d, J=8Hz), 6.92(1H, bd, J=8Hz), 7.5–7.8(8H, m), 7.88(1H, m) |

TABLE 1-continued

| Compound No. (process) | Substituent R¹—X R² \ Y—◯ / N | R³ | Z | m.p. (°C.) | NMR(100 MHz, δ) |
|---|---|---|---|---|---|
| 56 (a) | " | 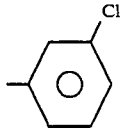 (phenyl with Cl) | " | 115–119 | (CDCl₃)1.30(3H, t, J=8Hz), 2.75(3H, s), 3.10 (2H, t, J=8Hz), 6.44(1H, d, J=8Hz), 7.20(1H, bd, J=8Hz), 6.62(4H, m) |
| 57 (a) | 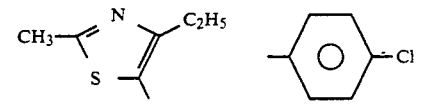 CH₃—(thiazole)—C₂H₅ | 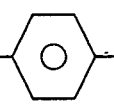 (phenyl-Cl) | CN | 146–148 | (CDCl₃)1.29(3H, t, J=8Hz), 2.73(3H, s), 3.08 (2H, q, J=8Hz), 6.40(1H, d, J=8Hz), 7.08(1H, bd, J=8Hz), 7.64(4H, s) |
| 58 (a) |  | 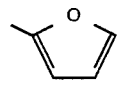 (furan) | " | oil | (CDCl₃)6.30(1H, d, J=8Hz), 6.1–6.62(2H, m), 7.18–7.46(1H, m), 8.14(1H bd, J=8Hz), 8.35 (1H, s), 8.86(1H, s) |
| 59 (a) | 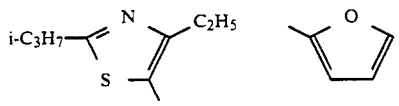 i-C₃H₇—(thiazole)—C₂H₅ | 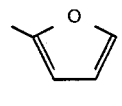 (furan) | " | 88–89 | (CDCl₃)1.28(3H, t, J=8Hz), 1.37(6H, d, J=7Hz), 3.03(2H, q, J=8Hz), 3.18(1H, sx, J=7Hz), 6.24 (1H, bd, J=7Hz), 6.33(1H, d, J=7Hz), 6.16–6.24 (2H, m), 7.28–7.52(1H, m) |
| 60 (a) | " | 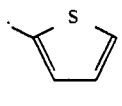 (thiophene) | " | 135–136 | (CDCl₃)1.30(3H, t, J=8Hz), 1.39(6H, d, J=7Hz), 3.06(2H, q, J=8Hz), 3.25(1H, qt, J=7Hz), 6.41 (2H, singlet like), 6.92–7.46(3H, m) |
| 61 (a) | " | 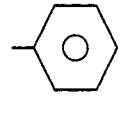 (phenyl) | " | 115–116 | (CDCl₃)1.29(3H, t, J=8Hz), 1.38(6H, d, J=6Hz), 3,05(2H, q, J=8Hz), 3.32(1H qt, J=6Hz), 6.25 (2H, singlet like), 7.20–7.60(5H, m) |
| 62 (a) | 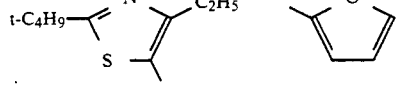 t-C₄H₉—(thiazole)—C₂H₅ | 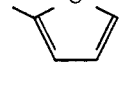 (furan) | " | 108.5–109.5 | (CDCl₃)1.28(3H, t, J=7Hz), 1.43(9H, s), 3.05 (2H, q, J=7Hz), 6.24(1H, d), 6.10–6.58(3H, m), 7.20–7.46(1H, m) |
| 63 (a) | 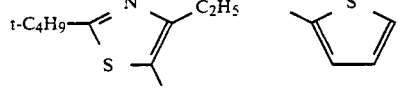 t-C₄H₉—(thiazole)—C₂H₅ | 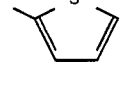 (thiophene) | CN | 145–146 | (CDCl₃)1.29(3H, t, J=8Hz), 1.43(9H, s), 3.06 (2H, q, J=8Hz), 6.39(2H, singlet like), 6.90–7.44(3H, m) |
| 64 (a) | " | 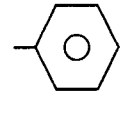 (phenyl) | " | 126–127 | (CDCl₃)1.30(3H, t, J=8Hz), 1.44(9H, s), 3.08 (2H, q, J=8Hz), 6.22(2H, singlet like), 7.20–7.64(5H, m) |
| 65 (a) | 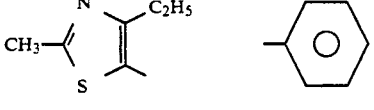 CH₃—(thiazole)—C₂H₅ | 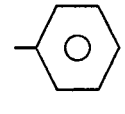 (phenyl) | " | 118–120 | (CDCl₃)1.26(3H, t, J=7Hz), 2.65(3H, s), 2.97 (2H, q, J=7Hz), 6.28(1H, d, J=8Hz), 6.46(1H, bd, J=8Hz), 7.0–7.6(4H, m) |
| 66 (a) | 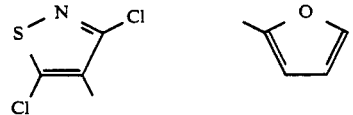 (isothiazole with Cl, Cl) | 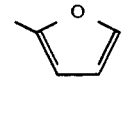 (furan) | " | semi-solid | (CDCl₃)6.28(1H, d, J=8Hz), 6.02–6.68(2H, m), 7.11(1H, bd, J=8Hz), 7.20–7.44(1H, m) |
| 67 (a) |  (thiazole with CH₃) | 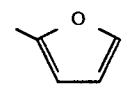 (furan) | " | 106–107 | (CDCl₃)2.89(3H, s), 6.36(1H, d, J=8Hz), 6.36–6.68(2H, m), 7.36–7.56(1H, m), 8.14(1H, bd, J=8Hz), 8.51(1H, s) |

TABLE 1-continued

| Compound No. (process) | Substituent (R¹-X, R², Y-N, R³ ring) | R³ | Z | m.p. (°C.) | NMR(100 MHz, δ) |
|---|---|---|---|---|---|
| 68 (a) | N=C(S-)(CH₃) thiazole-like with CH₃ | 2-thienyl (S) | " | 101–104 | (CDCl₃)2.86(3H, s), 6.44(1H, d, J=8Hz), 6.90–7.10(1H, m), 7.22–7.45(2H, m), 8.16(1H, bd, J=8Hz), 8.44(1H, s) |
| 69 (a) | same thiazole CH₃ | phenyl | CN | 94–94.5 | (CDCl₃)2.88(3H, s), 6.31(1H, d, J=8Hz), 7.30–7.68(5H, m), 8.15(1H, bd, J=8Hz), 8.46(1H, s) |
| 70 (a) | Cl–C=N, CH₃, S | 2-thienyl (S) | " | 128.0–129.0 | (CDCl₃)2.65(3H, s), 6.42(1H, d, J=8Hz), 6.76(1H, d, J=8Hz), 7.0–7.2(2H, m), 7.4(1H, s) |
| 71 (a) | Br–C=N, CH₃, S | 2-furyl (O) | " | 92.5–93.0 | (CDCl₃)2.70(3H, s), 6.31(1H, d, J=8Hz), 6.52(1H, dd, J=3.0, 1.0Hz), 6.55(1H, d, J=3.0Hz), 6.83(1H, d, J=8Hz), 7.55(1H, d, J=1Hz) |
| 72 (a) | " | 2-thienyl (S) | " | 131.5–132.0 | (CDCl₃)2.67(3H, s), 6.41(1H, d, J=8Hz), 6.77(1H, d, J=8Hz), 7.0–7.2(1H, m), 7.3–7.35(2H, m) |
| 73 (a) | I–C=N, CH₃, S | 2-furyl (O) | " | 130.5–131.0 | (CDCl₃)2.66(3H, s), 6.35(1H, d, J=8Hz), 6.62(1H, dd, J=3Hz, 1Hz), 6.71(1H, d, J=3Hz), 6.76(1H, d, J=8Hz), 7.52(1H, d, J=1Hz) |
| 74 (a) | " | 2-thienyl (S) | " | 130.5–131.0 | (CDCl₃)2.63(3H, s), 6.41(1H, d, J=8Hz), 6.77(1H, d, J=8Hz), 7.15(1H, m), 7.3–7.5(2H, m) |

The following Formulation Examples illustrate the preparation of the agricultural-horticultural fungicide or fungicidal composition of this invention. The active ingredient compounds are shown by the compound numbers given in Table 1. All parts are by weight.

FORMULATION EXAMPLE 1

Dust

Three parts of compound No 5, 20 parts of diatomaceous earth, 30 parts of terra alba, and 47 parts of talc were pulverized and mixed uniformly to obtain 100 parts of a dust.

FORMULATION EXAMPLE 2

Wettable powder

Thirty parts of compound No. 19, 47 parts of diatomaceous earth, 20 parts of terra alba, 1 part of sodium ligninsulfonate and 2 parts of sodium alkylbenzenesulfonate were uniformly pulverized and mixed to give 100 parts of a wettable powder.

FORMULATION EXAMPLE 3

Emulsifiable concentrate

Twenty parts of compound No. 6, 10 parts of cyclohexane, 50 parts of xylene and 20 parts of Sorpol (a trademark for a surface-active agent produced by Toho Chemical Co., Ltd.) were uniformly mixed to form 100 parts of an emulsifiable concentrate.

FORMULATION EXAMPLE 4

Granules

One part of compound No. 2, 78 parts of bentonite, 20 parts of talc and 1 part of sodium lignosulfonate were mixed, and a moderate amount of water was added, and the mixture was kneaded. The kneaded mixture was granulated by a customary method in an extrusion-granulation machine and dried to give 100 parts of granules.

FORMULATION EXAMPLE 5

Granules

Five parts of compound No. 11, 1 part of polyethylene glycol nonyl phenyl ether, 3 parts of polyvinyl alcohol and 91 parts of clay were uniformly mixed. Water was added, and the mixture was granulated and dried to give 100 parts of granules.

FORMULATION EXAMPLE 6

Dust

Two parts of compound No. 20, 40 parts of calcium carbonate and 58 parts of clay were uniformly mixed to give 100 parts of a dust.

FORMULATION EXAMPLE 7

Wettable powder

Fifty parts of compound No. 37, 40 parts of talc, 5 parts of sodium laurylphosphate and 5 parts of sodium alkylnaphthalenesulfonate were mixed to give 100 parts of a wettable powder.

FORMULATION EXAMPLE 8

Wettable powder

Fifty parts of compound No. 4, 10 parts of sodium lignosulfonate, 5 parts of sodium alkylnaphthalenesulfonate, 10 parts of white carbon and 25 parts of diatomaceous earth were mixed and pulverized to give 100 parts of a wettable powder.

FORMULATION EXAMPLE 9

Flowable agent

Forty parts of compound No. 10, 3 parts of carboxymethyl cellulose, 2 parts of sodium ligno-sulfonate, 1 part of dioctyl sulfosuccinate sodium salt and 54 parts of water were wet-pulverized by a sand grinder to give 100 parts of a flowable agent.

FORMULATION EXAMPLE 10

Dust

Two parts of compound No. 2, 2 parts of metalaxyl, 20 parts of diatomaceous earth, 30 parts of tetra alba and 45 parts of talc were mixed and pulverized to give 100 parts of a dust.

FORMULATION EXAMPLE 11

Wettable powder

Fifteen parts of compounds No. 4, 15 parts of oxadixyl, 47 parts of diatomaceous earth, 20 parts of terra alba, 1 part of sodium lignosulfonate and 2 parts of sodium alkylbenzenesulfonate were uniformly pulverized and mixed to give 100 parts of a wettable powder.

FORMULATION EXAMPLE 12

Wettable powder

10 Ten parts of compound No. 6, 20 parts of metalaxyl, 55 parts of talc, 3 parts of sodium laurylphosphate and 2 parts of sodium alkylnaphthalenesulfonate were mixed to give 100 parts of a wettable powder.

FORMULATION EXAMPLE 13

Wettable powder

Five parts of compound No. 2, 15 parts of ofurace, 65 parts of diatomaceous earth, 10 parts of white carbon, 3 parts of sodium laurylphosphate and 2 parts of sodium alkylnaphthalenesulfonate were mixed to give 100 parts of a wettable powder.

FORMULATION EXAMPLE 14

Wettable powder

Twenty parts of compound No. 2, 30 parts of benalaxyl, 35 parts of talc, 10 parts of white carbon, 3 parts of sodium laurylphosphate and 2 parts of alkylnaphthalenesulfonate were mixed to give 100 parts of a wettable powder.

FORMULATION EXAMPLE 15

Emulsifiable concentrate

Seven parts of compound No. 6, 10 parts of metalaxyl, 50 parts of phenoxyethanol, 28 parts of xylene, 3 parts of polyoxyethylene styryl phenyl ether and 2 parts of sodium alkylnaphthalenesulfonate were mixed to give 100 parts of an emulsifiable concentrate.

FORMULATION EXAMPLE 16

Granules

Three parts of compound No. 17, 10 parts of metalaxyl, 84 parts of clay, 1 part of polyethylene glycol nonylphenyl ether and 2 parts of polyvinyl alcohol were uniformly mixed and kneaded with the addition of a moderate amount of water. The kneaded mixture was granulated by a conventional method using an extrusion-granulator, and dried to give 100 parts of granules.

FORMULATION EXAMPLE 17

Wettable powder

Five parts of compound No. 4, 45 parts of mancozeb, 27 parts of diatomaceous earth, 20 parts of terra alba, 1 part of sodium lignosulfonate and 2 parts of sodium alkylbenzenesulfonate were pulverized and mixed uniformly to give 100 parts of a wettable powder.

FORMULATION EXAMPLE 18

Wettable powder

Ten parts of compound No. 18, 50 parts of mancozeb, 35 parts of talc, 3 parts of sodium laurylphosphate and 2 parts of sodium alkylnaphthalenesulfonate were uniformly pulverized and mixed to give 100 parts of a wettable powder.

FORMULATION EXAMPLE 19

Wettable powder

Five parts of compound No. 2, 50 parts of captan, 40 parts of talc, 3 parts of sodium laurylphosphate and 2 parts of sodium alkylnaphthalenesulfonate were uniformly pulverized and mixed to give 100 parts of a wettable powder.

FORMULATION EXAMPLE 20

Wettable powder

Ten parts of compound No. 2, 50 parts of captafol, 35 parts of talc, 3 parts of sodium laurylphosphate and 2 parts of sodium alkylnaphthalenesulfonate were pulverized and mixed uniformly to give 100 parts of a wettable powder.

FORMULATION EXAMPLE 21

Wettable powder

Five parts of compound No. 6, 50 parts of folpet, 40 parts of talc, 3 parts of sodium laurylphosphate and 2 parts of sodium alkylnapthalenesulfonate were uniformly pulverized and mixed to give a wettable powder.

FORMULATION EXAMPLE 22

Wettable powder

Five parts of compound No. 4, 50 parts of basic copper chloride, 40 parts of talc, 3 parts of sodium laurylphosphate and 2 parts of sodium alkylnaphthalenesulfonate were uniformly pulverized and mixed to give 100 parts of a wettable powder.

FORMULATION EXAMPLE 23

Wettable powder

Seven parts of compound No. 4, 50 parts of basic copper sulfate, 38 parts of talc, 3 parts of sodium laurylphosphate and 2 parts of sodium alkylnaphthalenesulfonate were uniformly pulverized and mixed to give 100 parts of a wettable powder.

FORMULATION EXAMPLE 24

Wettable powder

Five parts of compound No. 6, 50 parts of TPN, 40 parts of talc, 3 parts of sodium laurylphoaphate and 2 parts of sodium alkylnaphthalenesulfonate were uniformly pulverized and mixed to give 100 parts of a wettable powder.

FORMULATION EXAMPLE 25

Wettable powder

Seven parts of compound No. 2, 50 parts of zineb, 3 parts of sodium lignosulfonate, 3 parts of sodium alkylnaphthalenesulfonate, 7 parts of white carbon and 30 parts of diatomaceous earth were uniformly pulverized and mixed to give 100 parts of a wettable powder.

FORMULATION EXAMPLE 26

Wettable powder

Three parts of compound No. 2, 50 parts of mancozeb, 3 parts of sodium lignosulfonate, 3 parts of sodium alkylnaphthalenesulfonate, 5 parts of white carbon, 16 parts of terra alba and 20 parts of diatomaceous earth were uniformly pulverized and mixed to give 100 parts of a wettable powder.

FORMULATION EXAMPLE 27

Five parts of compound No. 10, 50 parts of dichlofluanide, 40 parts of talc, 3 parts of sodium laurylphosphate and 2 parts of sodium alkylnaphthalenesulfonate were uniformly pulverized and mixed to give 100 parts of a wettable powder.

FORMULATION EXAMPLE 28

Granules

One part of compound No. 2, 2 parts of polycarbamate, 85 parts of clay, 9 parts of diatomaceous earth, 1 part of polyethylene glycol nonyl-phenyl ether and 2 parts of polyvinyl alcohol were uniformly mixed, and further with the addition of a moderate amount of water, kneaded. The kneaded mixture was granulated by a conventional method in an extrusion-granulator and dried to give 100 parts of granules.

FORMULATION EXAMPLE 29

Dust

Two parts of compound No. 4, 20 parts of polycarbamate, 10 parts of diatomaceous earth, 20 parts of terra alba and 48 parts of talc were uniformly pulverized and mixed to give 100 parts of a dust.

The following Test Examples illustrate the efficacy of the compounds of this invention as the agricultural-horticultural fungicide and the agriculturalhorticultural fungicidal composition The compounds used in these test examples are indicated by the numbers shown in Table 1 or the symbols in Table 2.

TABLE 2

A: Complex of manganese and zinc ethylenebis(dithiocarbamates) [mancozeb]
B: zinc ethylenebis(dithiocarbamate) [zineb]
C: N-1',1',2',2'-tetracloroethylthio-4-cyclohexene-1,2-dicarboximide [captafol]
D: basic copper chloride
E: tetrachloroisophthalonitrile [TPN]
F: 3-chloro-N-(3-chloro-5-trifluoromethyl-2-pyridyl)-2,6-dinitro-4-trifluoromethylaniline [dichlofluanide]
G: N-(2,6-dimethylphenyl)-N-(2'-methoxyacetyl)alanine methyl ester [metalaxyl]
H: N-(2,6-dimethylphenyl)-N-(2-furoyl)alanine methyl ester [furalaxyl]
I: N-(2,6-dimethylphenyl)-N-(phenylacetyl)alanine methyl ester [benalaxyl]
J: 2-chloro-N-(2,6-dimethylphenyl)-N-(tetrahydro-2-oxo-3-furanyl)acetamide [ofurace]
K: 2-methoxy-N-(2,6-dimethylphenyl)-N-(2oxo-1,3-oxazolidin-3-yl)acetamide [oxadixyl]
L: 3-chloro-N-(oxoperhydro-3-furyl)-cyclopropanecarboxyanilide [cyprofuram]
M: N-(alpha-cyanofurfuryl)-2,6-dichloropyridine-4-carboxylic acid amide
N: N-(alpha-cyanofurfuryl)furane-2-carboxylic acid amide Note: Compounds M and N are described in the abovecited British Laid-Open Patent Application BP-2095237. Compounds G to L are commercial agricultural chemicals for controlling potato late blight and cucumber downy mildew.

TEST EXAMPLE 1

Test for controlling potato late blight (preventive effect):

A chemical (obtained by preparing a wettable powder of each test compound in accordance with the method of Formulation Example 8 and diluting it with water to a predetermined concentration) was applied to potato (variety: "danshaku"; plant height about 25 cm) grown in pots in a greenhouse at a rate of 50 ml per three pots by using a spray gun (1.0 kg/cm$^2$), and then dried in the air. A zoospore suspension of *Phytophthora infestans* cultured for 7 days on a potato slice was sprayed and inoculated on the potato plant. The test plant was maintained at a temperature of 17° to 19° C. and a humidity of more than 95% for 6 days, and then the degree of formation of lesions was examined.

The proportion of the area of lesions was observed and evaluated in each of the leaves, and the index of degree of the disease (disease index) was determined. In each of the test areas, the lesion index was calculated in accordance with the following equation.

$$\text{Lesion index} = \frac{4n_4 + 3n_3 + 2n_2 + 1n_1 + 0n_0}{N}$$

The standards of evaluation are as follows:

| Disease Index | Proportion of the area of lesion |
|---|---|
| 0 | 0% |
| 1 | 1–25% |
| 2 | 6–25 |
| 3 | 26–50 |
| 4 | 51% or more |

$n_0$: the number of leaves with a disease index of 0
$n_1$: the number of leaves with a disease index of 1
$n_2$: the number of leaves with a disease index of 2
$n_3$: the number of leaves with a disease index of 3
$n_4$: the number of leaves with a disease index of 4
$N = n_0 + n_1 + n_2 + n_3 + n_4$

TEST EXAMPLE 2

Test for controlling potato late blight (curative effect)

A zoospore suspension was prepared from *Phytophthora infestans* cultured for 7 days on a potato slice was inoculated by spraying on potato (variety: "danshaku"; plant height about 25 cm) grown in pots in a greenhouse. The pots were maintained at 17° to 19° C. for 20 hours, and then a chemical having a predetermined concentration (obtained by preparing a wettable powder of each test compound in accordance with the method of Formulation Example 8 and diluting it with water to the predetermined concentration) was sprayed onto the potato plants at a rate of 50 ml per three pots by using a spray gun (1.0 kg/cm$^2$), and then dried in the air. The pots were maintained at a temperature of 17° to 19° C. and a humidity of more than 95% for 6 days, and then the degree of formation of lesions was examined. The standards of evaluation and the method of indicating the lesion index were as shown in Test Example 1.

TEST EXAMPLE 3

Test for controlling cucumber downy mildew (preventive effect)

A chemical in a predetermined concentration (obtained by preparing a wettable powder of each test compound in accordance with the method of Formulation Example 8 and diluting it with water to the predetermined concentration) was sprayed on cucumber (variety: "Sagami hanjiro"; in the stage where two main leaves were developed) grown in pots in a greenhouse at a rate of 30 ml per three pots using a spray gun (1.0 kg/cm$^2$), and dried in the air. *Pseudoperonospora cubenis* were taken from the lesion of cucumber leaves infected with downy mildew and a spore suspension was prepared by using deionized water, and inoculated by spraying on the cucumber. Immediately then, the inoculated pots were maintained at a temperature of 18° to 20° C. and a humidity of more than 95% for 24 hours, and then transferred to a greenhouse (at 18° to 27° C.). Seven days later, the degree of formation of lesions was examined.

The standards of evaluation and the method of indicating the lesion index were as shown in Test Example 1.

TEST EXAMPLE 4

Test for controlling cucumber downy mildew 10 (curative effect)

As in Test Example 3, a spore suspension of *Pseudoperonospora cubenis* was prepared, and inoculated by spraying on the same cucumber as used in Test Example 3. Immediately then, the inoculated pots were maintained at a temperature of 18° to 20° C. and a humidity of more than 95% for 24 hours. A chemical in a predetermined concentration (obtained by preparing a wettable powder of each test compound in accordance with the method of Formulation Example 8 and diluting it with water to the predetermined concentration) was sprayed on the cucumber at a rate of 30 ml per three pots using a spray gun (1.0 kg/cm$^2$) and dried in the air. The pots were then transferred to a greenhouse (at 18° to 27° C.), and 7 days later, the degree of formation of lesions was examined.

The standards of evaluation and the method of indicating the lesion index were as shown in Test Example 1.

TEST EXAMPLE 5

Test for controlling tomato late blight (soil drench)

A chemical in a predetermined concentration (obtained by preparing a wettable powder of each test compound in accordance with the method of Formulation Example 8 and diluting it with water to the predetermined concentration) was drenched into the soil near the roots of tomato (variety: "sekaiichi"; height 20 cm) grown in pots (7.5 cm in diameter) in a greenhouse by mans of a pipette at a rate of 2 ml per pot. The pots were then maintained in the greenhouse for 5 days. A zoospore suspension was prepared from *Phytophthora infestans* cultured for 7 days on a potato slice. The suspension was then inoculated by spraying on the chamical-treated tomato plants. The test plants were maintained at a temperature of 17° to 19° C. and a humidity of more than 95%, and the degree of formation of lesions was examined.

The standards of evaluation and the method of indicating the lesion index were as shown in Test Example 1.

In the above Test Examples, the concentration of the active ingredients was adjusted to 100 ppm in the case of spraying, and to 15 g/acre in the case of soil drench.

The results of the above Test Examples are shown in Table 3.

TEST EXAMPLE 6

Test for controlling cucumber downy mildew (curative effect and residual effect)

*Pseudoperonospora cubenis* was taken from the lesions on the leaves of cucumber (variety: "Sagami hanjiro"; in the stage where three main leaves were developed) grown in pots in a greenhouse, and using deionzied water, a spore suspension of the fungus was prepared. The spore suspension was inoculated by spraying on the cucumber plants. The inoculated pots were maintained for 24 hours in the greenhouse, and a chemical in a predetermined concentration (obtained by preparing a wettable powder of each test compound in accordance with the method of Formulation Example 18 or 19 and diluting it to the predetermined concentration) at a rate of 50 ml per three pots by using a spray gun (1.0 kg/cm$^2$), and dried in the air. Then, the pots were transferred to a greenhouse (18° to 27° C.), and 10 and 18 days later, the degree of formation of lesions was examined. The results are shown in Table 4.

The standards of evaluation and the method of indicating the lesion index were as shown in Test Example 1.

TEST EXAMPLE 7

Test for controlling tomato late blight (curative effect and residual effect)

A zoospore suspension was prepared from *Phytophthora infestans* cultured on a potato slice for 7 days, and inoculated by spraying on tomato (variety: "sekaiichi"; plant height 20 cm) grown in pots in a greenhouse. The inoculated pots were maintained, for 24 hours in a humid chamber kept at 16° C., and a chemical in a predetermined concentration (obtained by preparing wettable powder of each test compound in accordance with Formulation Example 18 or 19, and diluting it with water to the predetermined concentration) was sprayed onto the plants at a rate of 50 ml per three pots by using a spray gun (1.0 kg/cm$^2$), and dried in the air. The pots were transferred to a greenhouse (10° to 20° C.), and 10 days and 11 days later, the degree of formation of lesions was examined. The results are shown in Table 5.

The standards of evaluation and the method of indicating the lesion index were as shown in Test Example 1.

TEST EXAMPLE 8

Test for controlling cucumber downy mildew (effect on a resistant strain to acylalanine chemicals)

A chemical in a predetermined concentration (obtained by preparing a wettable powder of each test compound in accordance with Formulation Example 11 or 12 and diluting it with water to the predetermined concentration) was sprayed onto cucumber (variety "Sagami hanjiro"; the stage where three main leaves were developed) grown in pots in a greenhouse at a rate of 50 ml per three pots by using a spray gun (1.0 kg/cm$^2$), and dried in the air. Each of *Pseudoperonospora cubenis* resistant and sensitive strain to acylalanine fungicide was taken from the lesions of cucumber leaves infected with downy mildew. They were mixed and a spore suspension was prepared from the mixture. The spore suspension was then inoculated on the treated cucumber leaves by spraying. The inoculated pots were maintained in a humid chamber at 20° C. for 24 hours, and then transferred to a greenhouse (18° to 27° C.) Ten days and 18 days later, the degree of formation of lesions was examined. The lesion index was determined as in Test Example 1. The results are shown in Table 6.

TEXT EXAMPLE 9

Test for controlling tomato early blight:

A chemical in a predetermined concentration (obtained by preparing a wettable powder of each test compound in accordance with Formulation Example 18 and diluting it with water to the predetermined concentration) was sprayed on tomato (variety: "sekaiichi"; plant height about 20 cm) grown in pots in a greenhouse at a rate of 50 ml per three pots by using a spray gun (1.0 kg/cm$^2$), and dried in the air. A spore suspension of *Alternaria solani* cultured in a PSA medium, and inoculated on tamato in the pots by spraying. The pots were transferred to a greenhouse (25° to 33° C.), and 10 days later, the degree of formation of lesions was examined. The lesion index was determined as in Test Example 1, and the results are shown in Table 7.

The results given in Table 3 demonstrate that the compounds of this invention shows a excellent control effect against plant diseases induced by Oomycetes, such as potato late blight, tomato late blight and cucumber downy mildew, not only in spraying but also in soil drench, whereas control compounds M and N considered to be relatively similar to the compounds of this invention show little or no control effect on these plant diseases. Furthermore, the compounds of this invention show a preventive effect at much lower dosages than zinc ethylenebis(dithiocarbmate) and tetrachloroisophthalonitrile commercially available and widely used against these plant diseases, and have a curative effect which these two commercial chemicals do not have. Accordingly, the compounds of this invention can exhibit a good control effect even when they are applied after crops have been infected with these diseases. Thus, this can greatly change the disease control system for agricultural and horticultural crops, and will evidently contribute greatly to labor saving on the part of the grower. Since the compounds of this invention have a good control effect when applied by soil drench, and enable that part of a plant which the chemical is not expected to reach by spraying alone to be protected from diseases.

The results given in Tables 4 and 5 show that the agricultural-horticultural fungicidal composition in accordance with this invention shows a very superior control effect at lower dosages than in the case of using the dithiocarbamates, N-haloalkylthioimides, inorganic copper fungicides, TPN, thiazole derivatives and isothiazole derivatives as the active ingredients. Evidently, the synergistic effect owing to mixing is noted and the residual effect is very much strengthened.

The results given in Table 7 show that the agricultural-horticultural fungicidal composition has an excellent control effect on a broad range of plant diseases induced by plant pathogenic fungi, such as *Alternaria solani, Pseudoperonospora cubenis* and *Colletotrichum lagenarium* which are taxonomically remote from each other. This means that in the cultivation of crops the application of the agricultural-horticultural fungicidal composition can control a plurality of simultaneously occurring plant diseases which are difficult to control simultaneously by conventional fungicidal compounds.

As shown in Table 6, the agricultural-horticultural fungicidal composition has an excellent control effect against a wide range of plant diseases induced by Oomycetes whose resistance to fungicidal chemicals is a serious problem. Specifically, the agricultural-horticultural fungicidal composition of this invention shows a much better control effect at lower dosages than in the case of singly using acylalanine fungicides (such as metalaxyl, furalaxyl, benalaxyl, oxadixyl, ofurace and cyprofuram), thiazoles derivatives and isothiazole derivatives, the active ingredients of this composition. Evidently, a synergistic effect is exhibited as a result of mixing.

TABLE 3

Test on diseases of potato, cucumber and tomato

| Test Compound No. | Potato late blight Preventive | Potato late blight Curative | Cucumber downy mildew Preventive | Cucumber downy mildew Curative | Tomato late blight Soil drain |
|---|---|---|---|---|---|
| 2 | 0 | 0 | 0 | 0 | 0 |
| 3 | 0 | — | 0 | 0 | 0 |
| 4 | 0 | 0 | 0 | 0 | 0 |
| 5 | 0 | 0 | 0 | 0 | 0 |
| 6 | 0 | — | 0 | 0 | 0 |
| 7 | 0 | 0 | 0 | 0 | 0 |
| 8 | 0.3 | — | 0.2 | 0 | 0.2 |
| 9 | 0 | 0 | 0 | 0 | 0 |
| 10 | 0 | — | 0 | 0 | 0 |
| 11 | 0 | 0 | 0 | 0 | 0 |
| 12 | 0 | 0 | 0 | 0 | 0 |
| 13 | 0 | — | 0 | 0 | 0 |
| 14 | 0 | 0 | 0 | 0 | 0 |
| 15 | 0 | 0 | 0 | 0 | 0 |
| 16 | 0 | — | 0 | 0 | 0 |
| 17 | 0 | 0 | 0 | 0 | 0 |
| 18 | 0 | — | 0 | 0 | 0 |
| 19 | 0 | 0 | 0 | 0 | 0 |
| 20 | 0 | 0 | 0 | 0 | 0 |
| 21 | 0 | — | 0 | 0 | 0 |
| 22 | 0 | 0 | 0 | 0 | 0 |
| 25 | 0 | — | 0 | 0 | 0 |
| 26 | 0 | 0 | 0 | 0 | — |
| 32 | 0 | 0 | 0 | 0 | 0 |
| 33 | 0 | 0 | 0 | 0 | 0 |
| 34 | 0 | 0 | 0 | 0 | 0 |
| 35 | 0 | 0 | 0 | 0 | 0 |
| 36 | 0 | — | 0 | 0 | 0 |
| 38 | 0 | 0 | 0 | 0 | — |
| 39 | 0 | — | 0 | 0 | 0 |
| 40 | 0 | 0 | 0 | 0 | — |
| 41 | 0 | — | 0 | 0 | 0 |
| 42 | 0.5 | 0.6 | 0.3 | 0.3 | — |
| 43 | 1.2 | — | 1.2 | 1.0 | — |
| 44 | 0 | 0 | 0 | 0 | — |
| 45 | 0 | 0 | 0 | 0 | — |
| 46 | 0 | — | 0 | 0 | 0 |
| 47 | 0 | 0 | 0 | 0 | — |
| 48 | 0 | 0 | 0 | 0 | — |
| 50 | 0 | 0 | 0 | 0 | 0 |
| 51 | 0 | 0 | 0 | 0 | 0 |

TABLE 3-continued

Test on diseases of potato, cucumber and tomato

| Test Compound No. | Potato late blight Preventive | Potato late blight Curative | Cucumber downy mildew Preventive | Cucumber downy mildew Curative | Tomato late blight Soil drain |
|---|---|---|---|---|---|
| 52 | 0 | 0 | 0 | 0 | 0 |
| 53 | 0 | 0 | 0 | 0 | 0 |
| 54 | 0 | 0 | 0 | 0 | 0 |
| 55 | — | — | 0 | 0.5 | — |
| 56 | — | — | 0.3 | 0.5 | — |
| 58 | 0 | — | 0 | 0 | — |
| 59 | 0 | 0 | 0 | 0 | 0 |
| 60 | 0 | 0 | 0 | 0 | — |
| 61 | 0 | 0 | 0 | 0 | — |
| 62 | 0 | 0.4 | 0 | 0 | — |
| 65 | — | — | 0 | 0 | — |
| 71 | — | — | 0 | 0.2 | — |
| 73 | — | — | 0 | 0.2 | — |
| M | 2.0 | 2.4 | 2.1 | 2.4 | 3.2 |
| N | 2.0 | 2.5 | 1.9 | 2.3 | 3.0 |
| B | 2.3 | 3.8 | 2.0 | 3.4 | 3.8 |
| E | 2.4 | 3.6 | 2.5 | 3.7 | 3.7 |
| Non-treated | 3.7 | 3.8 | 3.7 | 3.7 | 3.8 |

TABLE 4

Test on cucumber downy mildew

| Test compound No. | Concentration of the active ingredient (ppm) | Lesion index 10 days later | Lesion index 18 days later |
|---|---|---|---|
| 2 | 100 | 0 | 0.7 |
|  | 50 | 0 | 1.0 |
| 3 | 100 | 0 | 1.0 |
|  | 50 | 0 | 1.3 |
| 4 | 100 | 0 | 0.7 |
|  | 50 | 0 | 1.0 |
| 5 | 100 | 0 | 1.0 |
|  | 50 | 0 | 1.0 |
| 6 | 100 | 0 | 1.0 |
|  | 50 | 0 | 1.5 |
| 17 | 100 | 0 | 0.8 |
|  | 50 | 0 | 0.8 |
| 18 | 100 | 0 | 0.6 |
|  | 50 | 0 | 0.7 |
| A | 500 | 2.9 | 2.9 |
| C | 500 | 3.0 | 3.0 |
| D | 500 | 3.5 | 3.7 |
| E | 500 | 3.0 | 3.1 |
| F | 500 | 2.7 | 2.8 |
| 2 + A | 100 + 500 | 0 | 0 |
|  | 50 + 500 | 0 | 0 |
| 3 + A | 100 + 500 | 0 | 0 |
|  | 50 + 500 | 0 | 0 |
| 4 + A | 100 + 500 | 0 | 0 |
|  | 50 + 500 | 0 | 0 |
| 5 + A | 100 + 500 | 0 | 0 |
|  | 50 + 500 | 0 | 0 |
| 2 + C | 100 + 500 | 0 | 0 |
|  | 50 + 500 | 0 | 0 |
| 6 + C | 100 + 500 | 0 | 0 |
|  | 50 + 500 | 0 | 0 |
| 17 + C | 100 + 500 | 0 | 0 |
|  | 50 + 500 | 0 | 0 |
| 18 + C | 100 + 500 | 0 | 0 |
|  | 50 + 500 | 0 | 0 |
| 3 + D | 100 + 500 | 0 | 0 |
|  | 50 + 500 | 0 | 0.5 |
| 5 + D | 100 + 500 | 0 | 0 |
|  | 50 + 500 | 0 | 0.2 |
| 18 + D | 100 + 500 | 0 | 0.1 |
|  | 50 + 500 | 0 | 0.5 |
| 2 + E | 100 + 500 | 0 | 0 |
|  | 50 + 500 | 0 | 0 |
| 6 + E | 100 + 500 | 0 | 0 |
|  | 50 + 500 | 0 | 0 |
| 17 + E | 100 + 500 | 0 | 0 |

TABLE 4-continued

Test on cucumber downy mildew

| Test compound No. | Concentration of the active ingredient (ppm) | Lesion index 10 days later | Lesion index 18 days later |
|---|---|---|---|
|  | 50 + 500 | 0 | 0 |
| 18 + E | 100 + 500 | 0 | 0 |
|  | 50 + 500 | 0 | 0 |
| 2 + F | 100 + 500 | 0 | 0 |
|  | 50 + 500 | 0 | 0 |
| 4 + F | 100 + 500 | 0 | 0 |
|  | 50 + 500 | 0 | 0 |
| 5 + F | 100 + 500 | 0 | 0 |
|  | 50 + 500 | 0 | 0 |
| Non-treated | — | 3.7 | 3.7 |

TABLE 5

Test on tomato late blight

| Test compound No. | Concentration of the active ingredient (ppm) | Lesion index 10 days later | Lesion index 18 days later |
|---|---|---|---|
| 2 | 100 | 0 | 0.8 |
|  | 50 | 0 | 1.2 |
| 6 | 100 | 0 | 1.1 |
|  | 50 | 0 | 1.4 |
| 12 | 100 | 0 | 0.7 |
|  | 50 | 0 | 1.0 |
| 13 | 100 | 0 | 0.6 |
|  | 50 | 0 | 0.9 |
| 50 | 100 | 0 | 1.0 |
|  | 50 | 0 | 1.0 |
| 54 | 100 | 0 | 1.0 |
|  | 50 | 0 | 1.8 |
| A | 500 | 3.3 | 3.5 |
| C | 500 | 3.5 | 3.6 |
| D | 500 | 3.5 | 3.5 |
| E | 500 | 3.0 | 3.4 |
| F | 500 | 3.0 | 3.0 |
| 2 + A | 100 + 500 | 0 | 0 |
|  | 50 + 500 | 0 | 0 |
| 6 + A | 100 + 500 | 0 | 0 |
|  | 50 + 500 | 0 | 0 |
| 13 + A | 100 + 500 | 0 | 0 |
|  | 50 + 500 | 0 | 0 |
| 54 + A | 100 + 500 | 0 | 0 |
|  | 50 + 500 | 0 | 0.4 |
| 2 + C | 100 + 500 | 0 | 0 |
|  | 50 + 500 | 0 | 0 |
| 6 + C | 100 + 500 | 0 | 0 |
|  | 50 + 500 | 0 | 0 |
| 50 + C | 100 + 500 | 0 | 0 |
|  | 50 + 500 | 0 | 0 |
| 12 + D | 100 + 500 | 0 | 0.1 |
|  | 50 + 500 | 0 | 0.3 |
| 13 + D | 100 + 500 | 0 | 0 |
|  | 50 + 500 | 0 | 0 |
| 54 + D | 100 + 500 | 0 | 0.4 |
|  | 50 + 500 | 0.1 | 0.7 |
| 2 + E | 100 + 500 | 0 | 0 |
|  | 50 + 500 | 0 | 0.4 |
| 6 + E | 100 + 500 | 0 | 0 |
|  | 50 + 500 | 0 | 0 |
| 50 + E | 100 + 500 | 0 | 0 |
|  | 50 + 500 | 0 | 0 |
| 6 + F | 100 + 500 | 0 | 0 |
|  | 50 + 500 | 0 | 0 |
| 50 + F | 100 + 500 | 0 | 0 |
|  | 50 + 500 | 0 | 0 |
| 54 + F | 100 + 500 | 0 | 0 |
|  | 50 + 500 | 0 | 0 |
| Non-treated | — | 3.6 | 3.8 |

TABLE 6

Test on cucumber downy mildew

| Test compound No. | Concentration of the active ingredient (ppm) | Lesion index 10 days later | Lesion index 18 days later |
|---|---|---|---|
| 2 | 200 | 0 | 0.6 |
|  | 100 | 0 | 1.1 |
| 4 | 200 | 0 | 1.0 |
|  | 100 | 0 | 1.5 |
| 5 | 200 | 0 | 0.9 |
|  | 100 | 0 | 1.5 |
| 6 | 200 | 0 | 2.0 |
|  | 100 | 0.5 | 2.0 |
| G | 200 | 2.4 | 3.0 |
|  | 100 | 2.4 | 3.5 |
| H | 200 | 2.2 | 2.8 |
|  | 100 | 2.5 | 3.5 |
| I | 200 | 1.7 | 2.0 |
|  | 100 | 1.6 | 2.2 |
| J | 200 | 2.0 | 3.1 |
|  | 100 | 2.5 | 3.3 |
| K | 200 | 1.5 | 1.8 |
|  | 100 | 1.9 | 2.5 |
| L | 200 | 1.3 | 2.0 |
|  | 100 | 1.3 | 2.8 |
| 2 + G | 50 + 50 | 0 | 0 |
|  | 50 + 100 | 0 | 0 |
| 4 + G | 50 + 50 | 0 | 0 |
|  | 50 + 100 | 0 | 0 |
| 5 + G | 50 + 50 | 0 | 0 |
|  | 50 + 100 | 0 | 0 |
| 6 + G | 50 + 50 | 0 | 0 |
|  | 50 + 100 | 0 | 0 |
| 2 + H | 50 + 50 | 0 | 0 |
|  | 50 + 100 | 0 | 0 |
| 4 + H | 50 + 50 | 0 | 0 |
|  | 50 + 100 | 0 | 0 |
| 5 + H | 50 + 50 | 0 | 0 |
|  | 50 + 100 | 0 | 0 |
| 6 + H | 50 + 50 | 0 | 0.2 |
|  | 50 + 100 | 0 | 0.2 |
| 2 + I | 50 + 50 | 0 | 0 |
|  | 50 + 100 | 0 | 0 |
| 4 + I | 50 + 50 | 0 | 0 |
|  | 50 + 100 | 0 | 0 |
| 5 + I | 50 + 50 | 0 | 0 |
|  | 50 + 100 | 0 | 0 |
| 6 + I | 50 + 50 | 0 | 0.3 |
|  | 50 + 100 | 0 | 0.1 |
| 2 + J | 50 + 50 | 0 | 0 |
|  | 50 + 100 | 0 | 0 |
| 4 + J | 50 + 50 | 0 | 0 |
|  | 50 + 100 | 0 | 0 |
| 5 + J | 50 + 50 | 0 | 0 |
|  | 50 + 100 | 0 | 0 |
| 6 + J | 50 + 50 | 0 | 0.3 |
|  | 50 + 100 | 0 | 0.1 |
| 2 + K | 50 + 50 | 0 | 0 |
|  | 50 + 100 | 0 | 0 |
| 4 + K | 50 + 50 | 0 | 0 |
|  | 50 + 100 | 0 | 0 |
| 5 + K | 50 + 50 | 0 | 0 |
|  | 50 + 100 | 0 | 0 |
| 6 + K | 50 + 50 | 0 | 0.3 |
|  | 50 + 100 | 0 | 0.2 |
| 2 + L | 50 + 50 | 0 | 0 |
|  | 50 + 100 | 0 | 0 |
| 4 + L | 50 + 50 | 0 | 0 |
|  | 50 + 100 | 0 | 0 |
| 5 + L | 50 + 50 | 0 | 0 |
|  | 50 + 100 | 0 | 0 |
| 6 + L | 50 + 50 | 0 | 0 |
|  | 50 + 100 | 0 | 0 |
| Non-treated | — | 3.4 | 3.5 |

TABLE 7

Test on tomato early blight

| Test compound No. | Concentration of the active ingredient (ppm) | Lesion index |
|---|---|---|
| 2 | 100 | 2.6 |
| 3 | 100 | 3.0 |
| 4 | 100 | 3.1 |
| 6 | 100 | 3.0 |
| 12 | 100 | 2.7 |
| 18 | 100 | 2.9 |
| A | 500 | 0.8 |
| E | 500 | 0.7 |
| F | 500 | 1.0 |
| 2 + A | 100 + 500 | 0 |
| 3 + A | 100 + 500 | 0 |
| 12 + A | 100 + 500 | 0 |
| 4 + E | 100 + 500 | 0 |
| 6 + E | 100 + 500 | 0 |
| 18 + E | 100 + 500 | 0 |
| 2 + F | 100 + 500 | 0 |
| 3 + F | 100 + 500 | 0 |
| 12 + F | 100 + 500 | 0 |
| Non-treated | — | ? |

We claim:

1. An agricultural-horticultural fungicidal composition comprising a diluent or a carrier and/or an adjuvant, and as a first active ingredient (a) at least one amide derivative represented by the formula

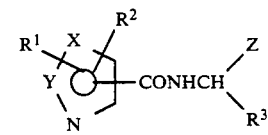

wherein X represents a sulfur atom and Y represents a carbon atom; Z represents a nitrile or thioamide group; each of $R^1$ and $R^2$ represents a hydrogen atom, a halogen atom, an alkyl group having 1 to 5 carbon atoms, or a phenyl group; and $R^3$ represents a furyl group or a thienyl group; and (b) as a second active ingredient at least one of acylalanine fungicide having the action of controlling plant diseases caused by Oomycetes, dithiocarbamate fungicides, N-haloalkylthioimide fungicides, inorganic copper fungicides, tetrachloroisophthalonitrile, dichlofluanide and fluazinam.

2. The composition of claim 1 in which the second active ingredient is at least one acylalanine fungicide having the action of controlling plant diseases caused by Oomycetes.

3. The composition of claim 1 in which the second active ingredient is at least one of dithiocabamate fungicides, N-haloalkylthioimide fungicides, inorganic copper fungicides, tetrachloroisophthalonitrile, dichlofulanide and fluazinam.

4. The composition of claim 1 in which the second active ingredient is a dithiocarbamate fungicide.

5. The composition of claim 1 in which the second active ingredient is an N-haloalkylthioimide fungicide.

6. The composition of claim 1 in which the second active ingredient is an inorganic copper fungicide.

7. The composition of claim 1 in which the first active ingredient is tetrachloroisophthalonitrile.

8. The composition of claim 1 in which the second active ingredient is dichlofluanide.

9. The composition of claim 1 in which the second active ingredient is fluazinam.

10. A method of controlling a plant disease, which comprises applying a fungicidal composition of claim 1 to plant pathogenic fungi or to their habitat in an amount of 0.2 to 5 kg/ha.

* * * * *